(12) United States Patent
Itoh et al.

(10) Patent No.: US 9,504,720 B2
(45) Date of Patent: Nov. 29, 2016

(54) SUBSTANCE FOR PREVENTING AND IMPROVING ARTHRITIS

(75) Inventors: Kikuji Itoh, Tokyo (JP); Shigeru Fujiwara, Kanagawa (JP)

(73) Assignee: Asahi Group Holdings, Ltd., Tokyo (JP)

( * ) Notice: Subject to any disclaimer, the term of this patent is extended or adjusted under 35 U.S.C. 154(b) by 461 days.

(21) Appl. No.: 13/983,488

(22) PCT Filed: Jan. 18, 2012

(86) PCT No.: PCT/JP2012/050889
§ 371 (c)(1),
(2), (4) Date: Aug. 2, 2013

(87) PCT Pub. No.: WO2012/105312
PCT Pub. Date: Aug. 9, 2012

(65) Prior Publication Data
US 2013/0316032 A1  Nov. 28, 2013

(30) Foreign Application Priority Data

Feb. 2, 2011 (JP) .................................. 2011-020765

(51) Int. Cl.
| | | |
|---|---|---|
| *A01N 63/02* | (2006.01) | |
| *A61K 35/00* | (2006.01) | |
| *C12N 1/00* | (2006.01) | |
| *C12N 1/20* | (2006.01) | |
| *A61K 35/74* | (2015.01) | |
| *A61K 31/198* | (2006.01) | |
| *A61K 31/20* | (2006.01) | |
| *A61K 31/7008* | (2006.01) | |
| *A61K 31/737* | (2006.01) | |
| *A61K 45/06* | (2006.01) | |
| *A61K 35/744* | (2015.01) | |
| *A23L 2/52* | (2006.01) | |

(52) U.S. Cl.
CPC ............... *A61K 35/74* (2013.01); *A23K 10/18* (2016.05); *A23L 2/52* (2013.01); *A23L 33/135* (2016.08); *A61K 31/198* (2013.01); *A61K 31/20* (2013.01); *A61K 31/7008* (2013.01); *A61K 31/737* (2013.01); *A61K 35/744* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 7,790,678 B1 * | 9/2010 | Girsh | .................... | A61K 31/683 424/9.1 |
| 2009/0028840 A1 * | 1/2009 | Im | ........................ | A23L 1/3014 424/93.45 |
| 2009/0196921 A1 * | 8/2009 | Ebel | ........................ | A61K 35/74 424/457 |
| 2010/0040735 A1 | 2/2010 | Fujiwara et al. | | |
| 2010/0041735 A1 | 2/2010 | Kandimalla et al. | | |
| 2010/0317835 A1 * | 12/2010 | Uede | .................... | C07K 14/8146 530/387.3 |
| 2011/0250189 A1 * | 10/2011 | Fujiwara | ............... | A23L 1/3014 424/93.45 |
| 2011/0300118 A1 * | 12/2011 | Hachimura | .......... | A61K 35/747 424/93.45 |

FOREIGN PATENT DOCUMENTS

| | | |
|---|---|---|
| JP | 09-503197 A | 3/1997 |
| JP | 2000-247895 A | 9/2000 |
| JP | 2004-091433 A | 3/2004 |
| JP | 2005-536197 A | 12/2005 |
| JP | 2005-537236 A | 12/2005 |
| JP | 2006-519014 A | 8/2006 |
| JP | 2007-210993 A | 8/2007 |
| JP | 2007-238581 A | 9/2007 |
| JP | 2007-269737 A | 10/2007 |
| JP | 2008-189572 A | 8/2008 |
| JP | 2008-530034 A | 8/2008 |
| JP | 2009-057346 A | 3/2009 |
| JP | 2009-114163 A | 5/2009 |
| JP | 2009-142266 A | 7/2009 |
| JP | 2009-269906 A | 11/2009 |
| WO | WO-2006/073145 A1 | 7/2006 |
| WO | WO-2006/093313 A1 | 9/2006 |
| WO | WO-2008/105540 A1 | 9/2008 |
| WO | WO 2009/101968 A1 | 8/2009 |

OTHER PUBLICATIONS

Hien Q. Huynh, MD et al., "Probiotic Preparation VSL#3 Induces Remission in Children with Mild to Moderate Acute Ulcerative Colitis: A Pilot Study", Inflamm Bowel Dis, vol. 15, No. 5, May 2009.
K Hatakka et al., "Effects of probiotic therapy on the activity and activation of mild rheumatoid arthritis—a pilot study", Scand J Rheumatol 2003; 32:211-215.
M.T. Nenonen et al., "Uncooked, Lactobacilli-Rich, Vegan Food and Rheumatoid Arthritis", British Journal of Rheumatology 1998; 37:274-281.
Pasi Kankaanpaa et al., " Homogenates derived from probiotic bacteria provide down-regulatory signals for peripheral blood mononuclear cells", Food Chemistry 83 (2003) 269-277. Accepted Feb. 11, 2003.

(Continued)

*Primary Examiner* — Chris R Tate
*Assistant Examiner* — Douglas F White
(74) *Attorney, Agent, or Firm* — Foley & Lardner LLP

(57) ABSTRACT

This application provides a substance containing disrupted cells of an anti-inflammatory lactic acid bacterium and having an effect of preventing or improving arthritis in a subject, a composition containing the substance and the preparation method thereof, and a method for enhancing the effect of preventing and improving arthritis with the use of the substance.

13 Claims, 9 Drawing Sheets

(56) References Cited

OTHER PUBLICATIONS

S. Kato et al., "Pathogenesis of nonsteroidal anti-inflammatory drug (NSAID)-induced small intestinal ulceration: aggravation of NSAID-provoked small intestinal ulceration in adjuvant-induced arthritis rats", Folia Pharmacol. Jpn. 133: 203-205 (2009).
Shinpei Torii et al., "Effects of Oral Administration of Lactobacillus acidophilus L-92 on the Symptoms and Serum Markers of Atopic Dermatitis in Children", Int Arch Allergy Immunol 211; 154:236-245, Published Online: Sep. 21, 2010.
Office Action dated May 7, 2015 in JP 2011-020765.
Fujimoto, M., "Antibody therapy targeting Th17 pathway: update—an anti-IL-12/23p40 antibody and an anti-IL-17 antibody," Experimental Medicine, 2010, 28(12):228-232, with partial English translation.
Fujio, K., Frontiers in Rheumatology & Clinical Immunology, 2010, 4(2):46-51, with partial English translation.
Miettinen et al., "Production of Human Tumor Necrosis Factor Alpha, Interleukin-6, and Interleukin-10 in Induced by Lactic Acid Bacteria," Infection and Immunity, Dec. 1996, 64(12):5403-5405.
Third Party Submission dated Jan. 6, 2015, in JP 2011-020765.
Lammers et al., "Immunomodulatory effects of probiotic bacteria DNA: IL-1 and IL-10 response in human peripheral blood mononuclear cells," FEMS Immunology and Medical Microbiology, 2003, 38:165-172.
Livshits et al., "Interleukin-6 is a Significant Predictor of Radiographic Knee Osteoarthritis," Arthritis & Rheumatism, Jul. 2009, 60(7):2037-2045.
Matsumoto et al., "Probiotic *Lactobacillus*-induced improvement in murine chronic inflammatory bowel disease is associated with the down-regulation of pro-inflammatory cytokines in lamina propria mononuclear cells," Clinical and Experimental Immunology, 2005, 140:417-426.
Stannus et al., "The association between leptin, interleukin-6, and hip radiographic osteoarthritis in older people: a cross-sectional study," Arthritis Research & Therapy, 2010, 12:R95, 1-9.

* cited by examiner

A    B

Test groups

★: p<0.05, ★★★: p<0.001
(vs each non-disrupted parent group)

★: p<0.05, ★★: p<0.01, ★★★: p<0.001
(vs Lactobacillus acidophilus CL-92)

SUBSTANCE FOR PREVENTING AND IMPROVING ARTHRITIS

CROSS-REFERENCE TO RELATED APPLICATIONS

This application is a national phase of PCT/JP2012/050889, filed Jan. 18, 2012, which was published on Aug. 9, 2012, as WO 2012/105312, which claims the benefit of Japanese Patent Application No. 2011/020765, filed Feb. 2, 2011. The respective contents of these applications are incorporated here by reference in their entirety.

TECHNICAL FIELD

The present invention relates to a substance for preventing and improving arthritis, and specifically a substance that essentially consists of the disrupted cells of an anti-inflammatory lactic acid bacterium or a mixture of the anti-inflammatory lactic acid bacterium and the disrupted cells thereof, a composition comprising the substance, and a method for producing the same.

BACKGROUND ART

Cells of specific lactic acid bacterial strains or bifidobacterial strains, and milk fermented with such bacterial cells, have been reported to be effective for amelioration of inflammation such as in the cases of allergy suppression, inflammatory bowel disease, and autoimmune disease (e.g., rheumatoid arthritis) (e.g., Patent Literatures 1-12, Non-patent Literature 1). The effect of improving arthritis in humans by intake of lactic acid bacteria has been verified and reported; however, there are few cases in which lactic acid bacteria exhibiting practically sufficient activity or usefulness have actually been applied. For example, the amount of a lactic acid bacterium to be taken is often large, and effectiveness is often evaluated under defective conditions of placebo controls, double blind tests, and experimental plans, in many literatures that demonstrate the effectiveness of intake of a lactic acid bacterium on humans (e.g., Non-patent Literatures 2 and 3). In addition, there are reports demonstrating that intake of a lactic acid bacterium does not improve arthritis (e.g., Non-Patent Literature 4). Based thereon, it has been speculated that the effect of improving arthritis by lactic acid bacteria is strain-specific, and thus selection is required. It has also been speculated that such lactic acid bacteria exhibit very weak activity when they are directly applied.

In recent years, cases of locomotive syndrome have been increasing due to changes in eating habits, lack of physical activities, age-related muscle weakness, joint inflammation, and the like. Patients with locomotive syndrome are highly likely to become bedbound, which poses large social problems. Major examples of such diseases include osteoarthritis and rheumatoid arthritis. However, adverse reactions such as small intestinal disease due not only to existing steroids, but also to anti-inflammatory agents that are nonsteroidal are major problems (Non-patent Literature 5, and Patent Literature 10, 13, and 14). As such, effective means for improving articular inflammation using safe immunoregulative materials such as lactic acid bacteria that can be orally taken within a practical dose range are still needed to prevent or treat articular inflammation.

PRIOR ART LITERATURE

Patent Literature

Patent Literature 1: JP Patent Publication (Kokai) No. 2009-269906 A
Patent Literature 2: International Patent Publication WO2006/093313
Patent Literature 3: JP Patent Publication (Kohyo) No. 2006-519014 A
Patent Literature 4: JP Patent Publication (Kohyo) No. 2005-537236 A
Patent Literature 5: JP Patent Publication (Kohyo) No. 2005-536197 A
Patent Literature 6: International Patent Publication WO2008/105540
Patent Literature 7: JP Patent Publication (Kokai) No. 2009-142266 A
Patent Literature 8: JP Patent Publication (Kohyo) No. 2008-530034 A
Patent Literature 9: JP Patent Publication (Kokai) No. 2009-57346 A
Patent Literature 10: JP Patent Publication (Kokai) No. 2004-091433 A
Patent Literature 11: JP Patent Publication (Kohyo) No. 2005-536197 A
Patent Literature 12: JP Patent Publication (Kokai) No. 2007-269737 A
Patent Literature 13: JP Patent Publication (Kokai) No. 2007-210993 A
Patent Literature 14: JP Patent Publication (Kokai) No. 2007-238581 A

Non-Patent Literature

Non-patent Literature 1: Int. Arch. Aller. Immunol. 54: 236-245, 2011
Non-patent Literature 2: Inflamm. Bowel Dis. 15(5): 760-768, 2009
Non-patent Literature 3: British J. Rheumatol. 37(3): 274-2811998
Non-patent Literature 4: Scand. J. Rheumatol. 32(4): 211215, 2003
Non-patent Literature 5: Folia Pharmacologica Japonica 133: 203-205, 2009, (Japan)

SUMMARY OF THE INVENTION

Problem to be Solved by the Invention

Regarding the inflammation-suppressing effect of specific bacteria belonging to lactic acid bacteria or bifidobacteria, specific bacterial species or strains are known to have such effects in patent publications or scientific articles concerning them. There are extremely few studies from the viewpoint of selecting and applying anti-inflammatory lactic acid bacteria and thus using highly active lactic acid bacteria. In terms of safety for oral administration (or intake), there are still high needs for lactic acid bacteria or bifidobacteria exhibiting anti-inflammatory effect, particularly prophylactic or therapeutic effect, on arthritis. However, there are almost no cases in which a processing technique of lactic acid bacteria has been developed in order to improve arthritis, and there are also almost no cases in which the use of a synergistic effect of a lactic acid bacterium and a known anti-inflammatory ingredient has been examined.

Under such circumstances, the present inventors have studied on enhanced effect of improving arthritis through the processing of anti-inflammatory lactic acid bacterial cells or the use of the synergistic effect thereof with other known anti-inflammatory ingredients.

Thus, an object of the present invention is to provide a substance for enhancing the effect of preventing or improving arthritis through the processing of anti-inflammatory lactic acid bacterial cells, and, a composition for preventing or improving arthritis that contains such substance.

Means for Solving the Problem

The present inventors have conducted extensive studies in order to solve the above problems. As a result, the present inventors have now incidentally and surprisingly discovered that the effect of suppressing, improving, or preventing arthritis in a subject is significantly exhibited or enhanced through disruption of lactic acid bacterial cells, thereby completing the present invention.

Accordingly, the present invention is as follows.
(1) A substance having both an effect of preventing or improving arthritis in a subject and the following properties (a) and (b):
(a) the substance is obtained by disrupting an anti-inflammatory lactic acid bacterium and contains about 5-100% by mass of disrupted cells relative to the lactic acid bacterial cells before disruption; and
(b) the substance has an effect of decreasing an expression level of IL-6 in a subject.
(2) The substance according to (1) above, containing about 20-100% by mass of disrupted cells relative to the lactic acid bacterial cells before disruption.
(3) The substance according to (1) or (2) above, wherein the average long diameter or surface area of each disrupted cell is 90% or less of that of the lactic acid bacterial cell before disruption.
(4) The substance according to any one of (1) to (3) above, wherein the substance has an effect of decreasing an expression level of IL-6 in the subject to 50% or less of that of disrupted cells before use.
(5) The substance according to any one of (1) to (4) above, wherein the anti-inflammatory lactic acid bacterium is characterized in that the expression level of Adam15, Stat3, or Cd40lg in the spleen tissue of an arthritis animal model satisfies at least one of the following conditions as a result of intake of the anti-inflammatory lactic acid bacterium:
expression of Adam15: less than 0.7;
expression of Stat3: 1.3 or more; and
expression of Cd40lg: less than 0.7,
when the original expression level of Adam15, Stat3, or Cd40lg in the spleen tissue of an arthritis animal model as a result of intake of a control non-anti-inflammatory substance is designated as 1.
(6) The substance according to any one of (1) to (5) above, wherein the disrupted cells have an effect of decreasing the expression level of FGF-basic in the subject compared with that before use of the disrupted cells.
(7) The substance according to any one of (1) to (6) above, wherein the disrupted cells are obtained by physical disruption, chemical treatment, or enzymatic lysis.
(8) The substance according to any one of (1) to (7) above, wherein the anti-inflammatory lactic acid bacterium is at least one bacterium belonging to a genus selected from the group consisting of the genera *Lactobacillus, Bifidobacterium, Enterococcus, Leuconostoc, Streptococcus, Lactococcus, Pediococcus*, and *Weissella*.
(9) The substance according to (8) above, wherein the bacterium belonging to the genus *Lactobacillus* is at least one bacterium selected from the group consisting of *Lactobacillus amylovorus, Lactobacillus gasseri, Lactobacillus casei, Lactobacillus paracasei, Lactobacillus zeae, Lactobacillus rhamnosus, Lactobacillus reuteri, Lactobacillus acidophilus, Lactobacillus crispatus, Lactobacillus gallinarum, Lactobacillus brevis, Lactobacillus fermentum, Lactobacillus plantarum, Lactobacillus delbrueckii* subsp. *bulgaricus*, and *Lactobacillus johnsonii*.
(10) The substance according to (8) above, wherein the bacterium belonging to the genus *Bifidobacterium* is at least one bacterium selected from the group consisting of *Bifidobacterium breve, Bifidobacterium longum, Bifidobacterium pseudolongum, Bifidobacterium animalis, Bifidobacterium adolescentis, Bifidobacterium bifidum, Bifidobacterium lactis, Bifidobacterium catenulatum, Bifidobacterium pseudocatenulatum*, and *Bifidobacterium magnum*.
(11) The substance according to (8) above, wherein the bacterium belonging to the genus *Enterococcus* is at least one bacterium selected from the group consisting of *Enterococcus faecalis* and *Enterococcus faecium*.
(12) The substance according to (8) above, wherein the bacterium belonging to the genus *Streptococcus* is at least one bacterium selected from the group consisting of *Streptococcus thermophiles, Streptococcus lactis, Streptococcus diacetilactis*, and *Streptococcus faecalis*.
(13) The substance according to (8) above, wherein the bacterium belonging to the genus *Leuconostoc* is at least one bacterium selected from the group consisting of *Leuconostoc mesenteroides* and *Leuconostoc lactis*.
(14) The substance according to (8) above, wherein the bacterium belonging to the genus *Lactococcus* is at least one bacterium selected from the group consisting of *Lactococcus lactis, Lactococcus plantarum*, and *Lactococcus raffinolactis*.
(15) The substance according to (8) above, wherein the bacterium belonging to the genus *Pediococcus* is at least one bacterium selected from the group consisting of *Pediococcus pentosaceus* and *Pediococcus damnosus*.
(16) The substance according to (8) above, wherein the bacterium belonging to the genus *Weissella* is at least one bacterium selected from the group consisting of *Weissella cibaria, Weissella confusa, Weissella halotolerans, Weissella hellenica, Weissella kandleri, Weissella kimchii, Weissella koreensis, Weissella minor, Weissella paramesenteroides, Weissella soli, Weissella thailandensis*, and *Weissella viridescens*.
(17) The substance according to any one of (1) to (16) above, wherein the arthritis is rheumatoid arthritis, knee osteoarthritis, tenosynonitis, periomarthritis, tendinitis, or coxitis.
(18) A composition for preventing or improving arthritis, comprising the substance according to any one of (1) to (17) above.
(19) The composition according to (18) above, further comprising at least one known substance having an anti-inflammatory effect.
(20) The composition according to (19) above, wherein the known substance having an anti-inflammatory effect is collagen, glucosamine, chondroitin, fatty acid, amino acid, or a salt thereof, or a combination thereof.
(21) The composition according to (20) above, wherein the combination is with glucosamine or a salt thereof and chondroitin or a salt thereof.
(22) The substance or the composition according to any one of (18) to (21) above, wherein the arthritis is rheumatoid arthritis, knee osteoarthritis, tenosynonitis, periomarthritis, tendinitis, or coxitis.
(23) A product comprising, as an active ingredient, the substance of any one of (1) to (17) above or the composition of any one of (18) to (22) above.

(24) The product according to (23) above, which is a food or drink, a feedstuff, or a medicament.

(25) A method for producing a product for improving a disease or disorder associated with articular inflammation, comprising incorporating the substance of any one of (1) to (17) above or the composition of any one of (18) to (22) above into a food or drink, a feedstuff, or a medicament.

(26) A method for enhancing the effect of preventing or improving arthritis, comprising, upon production of a food or drink, a feedstuff, or a pharmaceutical product for preventing or improving arthritis, incorporating the substance of any one of (1) to (17) above and at least one known substance having an anti-inflammatory effect.

(27) The method according to (26) above, wherein the known substance having an anti-inflammatory effect is collagen, glucosamine, chondroitin, a fatty acid, an amino acid, or a salt thereof, or a combination of any thereof.

(28) The method according to (27) above, wherein the combination is of glucosamine or a salt thereof, and, chondroitin or a salt thereof.

This description includes all or part of the contents as disclosed in the description and/or drawings of Japanese Patent Application No. 2011-020765, from which the present application claims the a priority.

Advantage of the Invention

According to the present invention, as described above, disrupted cells obtained by subjecting an anti-inflammatory lactic acid bacterium to disruption treatment enhances the effect of improving inflammation, and particularly arthritis. A substance containing such disrupted cells has high safety and also provides an action effect by which the symptoms of arthritis, such as rheumatoid arthritis that is an autoimmune disease, can be more significantly improved than intake of lactic acid bacterial cells themselves through reduction of inflammation-related cytokines, such as inflammatory cytokines and synovial membrane growth factors, and, through suppression of the activation of antigen presenting cells such as dendritic cell or macrophage.

BRIEF DESCRIPTION OF THE DRAWINGS

As shown in FIG. 1, cells were disrupted into small portions after disruption treatment.

EMBODIMENT FOR CARRYING OUT THE INVENTION

Figure 1:
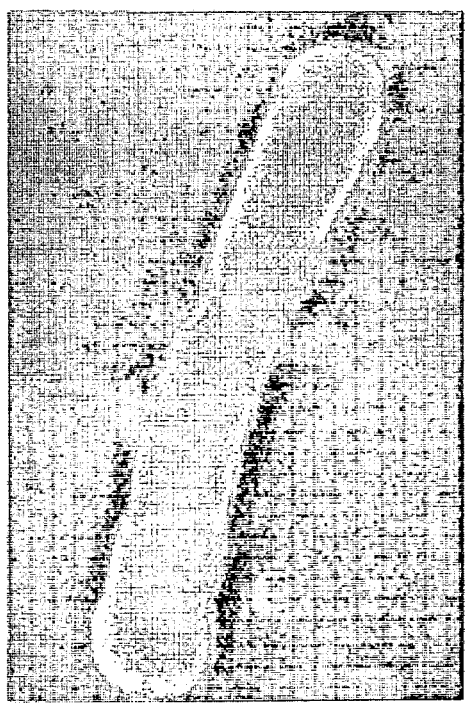
FIG. 1 shows electron micrographs of: (A) an intact cell before disruption treatment of lactic acid bacteria; and (B) a cell after disruption treatment.
Figure 1:
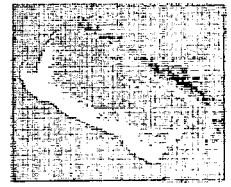

Hereafter, the present invention is described in detail.

1. Disrupted Cells of Anti-Inflammatory Lactic Acid Bacterium

The present invention is based on a finding that the effect of improving arthritis of a lactic acid bacterium can be exhibited or enhanced by disrupting cells of the anti-inflammatory lactic acid bacterium.

Thus, the present invention provides, in a first aspect, a substance having the following characteristics (a) and (b), and, having the effect of preventing or improving arthritis in a subject (as used herein, the term "substance having the effect of preventing or improving" can also be referred to as "agent for preventing or improving.").

(a) The substance is obtained by disrupting an anti-inflammatory lactic acid bacterium, containing about 5% to 100% by mass of disrupted cells of the anti-inflammatory lactic acid bacterium relative to the lactic acid bacterium before disruption.

(b) The substance has the effect of decreasing the expression level of IL-6 in a subject.

The above substance of the present invention can be used as an "additive" or an "additive agent" for a food or drink, a feedstuff, or a medicament, and thus can also be referred to as such. Specifically, the substance can also be referred to as a food additive, a feedstuff additive, or the like.

The content of disrupted cells of a lactic acid bacterium in the substance of the present invention, which is effective for improving arthritis, ranges from about 5% to 100% by mass, about 8% to 100% by mass, about 10% to 100% by mass, about 15% to 100% by mass, about 20% to 100% by mass, about 30% to 100% by mass or about 40% to 100% by mass, preferably about 50% to 100% by mass or about 60% to 100% by mass, more preferably about 70% to 100% by mass, about 80% to 100% by mass, or about 90% to 100% by mass relative to the undisrupted lactic acid bacterium cells before disruption. The effect of improving arthritis tends to increase as the content of disrupted cells increases. The most preferable content of the disrupted cells ranges from about 90% to 100% by mass.

The term "anti-inflammatory lactic acid bacterium" as used herein refers to, in the present invention, a lactic acid bacterium exhibiting the effect of suppressing or improving inflammation, and particularly arthritis. Specifically, a lactic acid bacterium (strain) is administered to an arthritis animal model (e.g., rat or mouse) and then an anti-inflammatory lactic acid bacterium can be selected by measuring the expression level of a factor involved in inflammation or immune system, in body fluid such as blood (e.g., blood plasma or serum) or joint fluid, or a tissue of spleen, Peyer's patch, or joint. Specifically, an anti-inflammatory lactic acid bacterium that can be used in the present invention is characterized in that, when the expression level of a non-anti-inflammatory control substance in spleen tissue of an arthritis animal model upon intake of the control substance is designated as 1, the expression level of Adam15 (tissue metalloprotease), Stat3 (transcription factor), or Cd40lg (Cd40 ligand) in spleen tissue of the arthritis animal model upon intake of the anti-inflammatory lactic acid bacterium satisfies at least one of the following conditions.

Expression of Adam15: less than 0.7 (suppressed)
(the expression level of Adam15 is preferably less than 0.5, and more preferably less than 0.25.)
Expression of Stat3: 1.3 or more (increased)
(The expression level of Stat3 is preferably 1.5 or more, and more preferably 1.75 or more.)
Expression of Cd40lg: less than 0.7 (suppressed)
(The expression level of Cd40lg is preferably less than 0.5 and more preferably less than 0.25.)

Regarding production of an arthritis animal model, an animal model having adjuvant arthritis can be produced by intradermally injecting Freund's complete adjuvant to a footpad of a hindlimb of an animal such as rat or mouse. Moreover, a rheumatoid arthritis animal model can be produced by deleting or knocking out the IL-1Ra gene in an animal (R. Horai et al, (2000). Development of chronic inflammatory arthropathy resembling rheumatoid arthritis in interleukin 1 receptor antagonist-deficient mice. J. Exp. Med, 191: 313-320).

The non-anti-inflammatory control substance may be any substance as long as it is known to have no anti-inflammatory effect. Examples thereof include feeds for animal models and non-anti-inflammatory lactic acid bacteria.

Lactic acid bacteria produce lactic acid from saccharides through fermentation, most of which possess high safety. Anti-inflammatory lactic acid bacteria that can be used in the present invention satisfy the above defined conditions. Examples thereof include, but are not limited to, bacteria belonging to the genus *Lactobacillus, Leuconostoc, Lactococcus, Pediococcus, Enterococcus, Bifidobacterium, Streptococcus*, or *Weissella*. In the present invention, lactic acid bacterial strains known in the art can also be used in the present invention, as long as the disrupted cells thereof exhibit the effect of improving arthritis. In addition, bacterial strains that are preferably used herein have been confirmed to be safe for animals upon administration thereof to or intake thereof by animals.

Examples of anti-inflammatory lactic acid bacteria that can be used in the present invention are listed below.

Lactic acid bacteria belonging to the genus *Lactobacillus* are Gram-positive bacilli. Examples of such lactic acid bacteria include *Lactobacillus amylovorus, Lactobacillus gasseri, Lactobacillus casei, Lactobacillus paracasei, Lactobacillus zeae, Lactobacillus rhamnosus, Lactobacillus reuteri, Lactobacillus acidophilus, Lactobacillus crispatus, Lactobacillus gallinarum, Lactobacillus brevis, Lactobacillus fermentum, Lactobacillus plantarum, Lactobacillus delbrueckii* subsp. *bulgaricus*, and *Lactobacillus johnsonii*.

Lactic acid bacteria belonging to the genus *Bifidobacterium* are Gram-positive obligate anaerobic bacilli and are also referred to as bifidobacteria. Examples of such lactic acid bacteria include *Bifidobacterium breve, Bifidobacterium longum, Bifidobacterium pseudolongum, Bifidobacterium animalis, Bifidobacterium adolescentis, Bifidobacterium bifidum, Bifidobacterium lactis, Bifidobacterium catenulatum, Bifidobacterium pseudocatenulatum*, and *Bifidobacterium magnum*.

Lactic acid bacteria belonging to the genus *Enterococcus* are Gram-positive cocci. Examples of such lactic acid bacteria include *Enterococcus faecalis, Enterococcus hirae*, and *Enterococcus faecium*.

Among bacteria belonging to the genus *Streptococcus*, lactic acid bacteria are known to enable production of fermented milk such as yogurt. Examples of such lactic acid bacteria include *Streptococcus thermophilus, Streptococcus lactis, Streptococcus diacetilactis*, and *Streptococcus faecalis*.

Lactic acid bacteria belonging to the genus *Leuconostoc* are Gram-positive cocci and can be isolated from fermented plant products. Examples of such lactic acid bacteria include *Leuconostoc mesenteroides* and *Leuconostoc lactis*.

Lactic acid bacteria belonging to the genus *Lactococcus* are Gram-positive cocci, and are used for producing fermented milk products. Examples of such lactic acid bacteria include *Lactococcus lactis, Lactococcus plantarum, Lactococcus raffinolactis*, and *Lactococcus cremoris*.

Lactic acid bacteria belonging to the genus *Pediococcus* are Gram-positive cocci and can be isolated from fermented plant products. Examples of such lactic acid bacteria include *Pediococcus pentosaceus* and *Pediococcus damnosus*.

Examples of lactic acid bacteria belonging to the genus *Weissella* include *Weissella cibaria, Weissella confusa, Weissella halotolerans, Weissella hellenica, Weissella kandleri, Weissella kimchii, Weissella koreensis, Weissella minor, Weissella paramesenteroides, Weissella soli, Weissella thailandensis*, and *Weissella viridescens*.

Specific strains of the above exemplified lactic acid bacterial species may be any of strains isolated from nature, deposited strains, preserved strains, and commercially available strains, for example.

The term "effect of improving arthritis" or "arthritis improving effect" as used herein refers to the effect of suppressing or alleviating joint pain, or, the effect of improving arthritis. The term is specifically intended to indicate the effect of decreasing a blood inflammatory cytokine level, the effect of suppressing the abnormal growth of synovial membrane, and the normalization of the functions of joint tissue, as a result of the recovery of cartilage tissue. The effect of improving articular inflammation can be determined by, for example, measuring inflammatory cytokines (e.g., IL-6, FGF-basic, TNF-α, VEGF, and IL-1), inhibitory cytokines (e.g., IL-10 and TGF-β, and inflammation-related indicators (e.g., MAP kinase, tissue metalloprotease (Adam-15), and prostaglandin), in addition to be aware of a pain or swelling.

A disrupted product (cells) of the present invention has, as described in Examples later, (i) the effect of decreasing the expression level of IL-6 (articular inflammatory cytokine) in blood or joint fluid, and furthermore, the expression level of FGF-basic (also referred to as "b-FGF"), compared with those in a subject before use of the disrupted product in the subject, and/or, (ii) the effect of increasing the expression level of Stat3 (transcription factor) in spleen tissue, compared with that in a subject before use of the disrupted product, and/or, (iii) the effect of suppressing the expression levels of the genes of Adam-15, Cd40lg, and the like in spleen tissue, and the expression levels of the genes of Il-22, Il22ra1, and the like in Peyer's patch, compared with those in the subject before use of the disrupted product.

The expression level of IL-6 in the above subject can be decreased to generally 50% or less, preferably 40% or less, and further preferably 30% or less compared with that before use of the disrupted product (cells). Moreover, the expression level of FGF-basic in the above subject can be decreased to generally 40% or less, preferably 30% or less, and further preferably 20% or less compared with that before use of the disrupted product.

IL-6 is excessively present in a blood sample or a joint fluid of a patient with a disease associated with articular inflammation, such as rheumatoid arthritis (Hirano, T. et al., Eur. J. Immunol., 1988; 18: 1797-1801). IL-6 is one of causative substances that induce the onset or the exacerbation of symptoms of arthritis. An anti-IL-6 receptor antibody that suppresses the functions of IL-6 has been approved in Japan as a therapeutic agent for rheumatoid arthritis. FGF-basic is also one of important factors involved in synovial cell proliferation that causes joint destruction. Suppression of the function of FGF-basic may improve arthritis. The disrupted product (cells) of the present invention has the effect of significantly suppressing the expression of IL-6 and FGF-basic, and thus it also has the effect of improving diseases associated with articular inflammation. Surprisingly, such improvement effect can further be enhanced by combining the disrupted product of the present invention with a known substance(s) having an anti-inflammatory effect (e.g., collagen, glucosamine, chondroitin, fatty acids, amino acids, salts thereof, or a combination thereof).

The expression levels of Adam-15, Stat3, Cd40lg, Il-22, and Il22ra1 after administration or intake of the disrupted product (cells) of the present invention are as described above. Specifically, when the expression level before use of the disrupted product is designated as 1, the expression level of Adam-15 is less than 0.7, preferably less than 0.5, and further preferably less than 0.25, the expression level of Stat3 is 1.3 or more, preferably 1.5 or more, and further preferably 1.75 or more, the expression level of Cd40lg is less than 0.7, preferably less than 0.5, and further preferably less than 0.25, and the expression levels of Il-22 and Il22ra1 are each less than 0.7, preferably less than 0.6, and further preferably less than 0.5.

Whether or not disrupted cells of a specific lactic acid bacterium have the effect of improving arthritis can be judged, evaluated (or obtaining data for evaluation), or determined by preparing disrupted cells of a lactic acid bacterium, orally administering the disrupted cells to subject animals such as experimental animals (e.g., arthritis animal model (e.g., mice or rats)) or causing the subject animals to take the disrupted cells, and then measuring the above indicators in subject animals.

Accordingly, in the present invention, any lactic acid bacterium can be used, as long as disrupted cells thereof have been evaluated as having the effect of improving arthritis by the above-mentioned evaluation method. Examples of preferable lactic acid bacteria having the effect of improving arthritis include, but are not limited to, *Lactobacillus amylovorus* CP1563 strain (FERM BP-11255; international deposition date: May 25, 2010), *Lactobacillus amylovorus* such as registration numbers JCM1029, JCM1032, and JCM1126 available from RIKEN BioResource Center-Japan Collection of Microorganisms (305-0074, 3-1-1, Takanodai, Tsukuba, Ibaraki, Japan), *Lactobacillus gasseri* CP2305 strain (FERM BP-11331; international deposition date: Sep. 11, 2007), *Lactobacillus gasseri* such as registration numbers JCM1017, JCM1019, JCM1025, and JCM1131 available from RIKEN BioResource Center, *Lactobacillus acidophilus* CL-92 strain (FERM BP-4981; international deposition date: Mar. 3, 1994), *Lactobacillus acidophilus* such as registration numbers JCM1021, JCM1039, and JCM1132 available from RIKEN BioResource Center, *Lactobacillus casei* such as *Lactobacillus casei* SP1 strain (isolate from human (Japanese) feces; see FIG. 2), *Lactobacillus rhamnosus* such as *Lactobacillus rhamnosus* SP1 strain, *Lactobacillus paracasei* such as *Lactobacillus paracasei* SP1 (isolate from human (Japanese) feces; see FIG. 2), *Lactobacillus crispatus* such as registration numbers JCM1030, JCM1185, and JCM2009 available from RIKEN BioResource Center, *Lactobacillus gallinarum* such as registration numbers JCM1036, JCM2011, and JCM8782 available from RIKEN BioResource Center, *Lactobacillus johnsonii* such as registration numbers JCM1022, JCM2012, and JCM2122 available from RIKEN BioResource Center, *Bifidobacterium pseudocatenulatum* such as *Bifidobacterium pseudocatenulatum* SP1 strain (isolate from human (Japanese) feces; see FIG. 2), and *Bifidobacterium longum* such as *Bifidobacterium longum* SP1 strain (isolate from human (Japanese) feces; see FIG. 2).

In addition, some of the above lactic acid bacterial strains are human intestinal tract-derived lactic acid bacteria. The above strains indicated with "FERM BP-" have been confirmed, as described in Examples later, such that the disrupted cells thereof have the effect of improving arthritis. Moreover, the strains have been internationally deposited with the International Patent Organism Depositary, the National Institute of Advanced Industrial Science and Technology (AIST) (Tsukuba Central 6, 1-1-1 Higashi, Tsukuba, Ibaraki, 305-8566, Japan), which is an international depository authority established under the Budapest Treaty for deposition of patent microorganisms.

Furthermore, in the present invention, mutant strains prepared from or strains derived from the above-mentioned specific strains can be used, as long as they have the effect of improving arthritis. Whether or not such a mutant strain or a strain derived from the above-mentioned specific strain has the effect of improving arthritis can be confirmed by exposing a parent culture strain to a mutagen such as a nitrosourea derivative (e.g., N-methyl-N-nitrosourea or N-ethyl-N-nitrosourea), nitrosoguanidine, or nitrosoamine or a high energy ray such as ultraviolet ray, X ray, or γ ray, collecting colonies, culturing cells by pure culture, and then evaluating the resultant using the above evaluation method.

An anti-inflammatory lactic acid bacterium can be prepared by culturing it using a medium that is generally used for culturing lactic acid bacteria under appropriate conditions. Either natural or synthetic medium can be used for culture, as long as it contains carbon sources, nitrogen sources, inorganic salts, and the like and enables efficient culture of lactic acid bacteria. Persons skilled in the art can adequately select a known medium appropriate for a bacterial strain to be used herein.

As carbon sources, for example, lactose, glucose, sucrose, fructose, galactose, and molasses can be used. As nitrogen sources, organic nitrogen-containing substances such as a casein hydrolysate, a whey protein hydrolysate, and a soybean protein hydrolysate can be used. Furthermore, as inorganic salts, phosphate, sodium, potassium, magnesium, and the like can be used. Examples of a medium appropriate for culturing lactic acid bacteria include an MRS liquid medium, a GAM mdium, a BL medium, Briggs Liver Broth, animal milk, skimmed milk, and milk whey. Preferably, a sterilized MRS medium can be used. As a natural medium, tomato juice, carrot juice, or another type of vegetable juice, or apple, pineapple, or grape fruit juice can be used as ingredients of food-grade media, for example.

In addition, lactic acid bacteria can be cultured at a temperature of 20° C. to 50° C., preferably 25° C. to 42° C., and more preferably approximately 37° C. under anaerobic conditions. Temperature conditions can be adjusted using a thermostat bath, a mantle heater, a jacket, or the like. The term "anaerobic conditions" as used herein refers to a low-oxygen environment in which lactic acid bacteria can proliferate. For example, anaerobic conditions can be provided by using an anaerobic chamber, anaerobic box, or airtight container or bag containing a deoxidizer, or by simply sealing a culture container. Examples of culture formats include static culture, shake culture, and tank culture. The period of culture can be 3 hours to 96 hours. It is preferable to maintain the pH of a medium in the beginning of culture at 4.0 to 8.0.

Specific examples of preparation of lactic acid bacteria are as briefly described below.

For example, when lactic acid bacteria of the genus *Lactobacillus* such as *Lactobacillus amylovorus* CP1563 strain, *Lactobacillus gasseri* CP2305 strain, and *Lactobacillus acidophilus* CL-92 strain are used as anti-inflammatory lactic acid bacteria, a lactic acid bacterium is seeded into a food-grade medium for culturing lactic acid bacteria and then the lactic acid bacterium can be cultured overnight (about 18 hours) at about 37° C.

After culture, the obtained culture of a lactic acid bacterium may be directly used, or if needed, the obtained culture may be further subjected to, for example, crude purification using centrifugation and/or solid-liquid separation using filtration, and to sterilization. Preferably, the lactic acid bacterial cells alone are collected via centrifugation. Lactic acid bacteria to be used in the present invention may be in the form of either wet cells or dried cells (e.g., via lyophilization).

In the present invention, disrupted cells of an anti-inflammatory lactic acid bacterium can be used as active ingredients for preventing or improving arthritis.

The term "disrupted product (or disrupted cells)" as used herein refers to damaged cells, including cells damaged by disruption, grinding, crushing, or the like. Preferably such a disrupted product comprises all solid and liquid components of cells obtained by disruption. Regardless of a disruption method, examples of the disrupted product can include a water-soluble fraction, an organic solvent-soluble fraction, an organic solvent- or water-poorly soluble fraction, and an organic solvent- or water-insoluble fraction obtained after damage of cells. Such a disrupted product can also be obtained by disrupting cells and then lyophilizing all solid and liquid components.

Dry powders of a lactic acid bacterium prepared by simply drying the bacterium by a technique such as lyophilization have a very low degree of disruption of cells (proportion of disrupted cells: less than 0.01% by mass). Such dried product does not correspond to a substance containing the disrupted cells of the present invention. To obtain a disrupted product (cell) that can be used in the present invention, lactic acid bacteria should actually be subjected to a disruption step.

Cells can be disrupted by using methods and apparatuses known in the art, and examples of damaging include, but are not limited to, physical disruption, enzymatic lysis treatment, chemical treatment, and autolysis treatment.

Physical disruption may be carried out by using either a wet system (which is a treatment conducted in the state of a cell suspension) or a dry system (which is a treatment carried out in the state of a cell powder). The physical disruption may be carried out by agitation using, for example, homogenizer, ball mill, bead mill, or satellite mill, or by pressure application using, for example, jet mill, French press, or cell disruptor, or by filtration using a filter.

Enzymatic lysis treatment is carried out by disrupting cell walls of lactic acid bacteria using an enzyme such as lysozyme.

Chemical treatment is carried out by disrupting the cellular structures of lactic acid bacteria using a surfactant such as a glycerin ester of fatty acid and soybean phospholipid.

Autolysis is carried out by degrading cells by a lactic acid bacterium's own enzyme(s).

In the present invention, physical disruption is preferred since addition of other reagents or ingredients is not required.

For example, when physical disruption is performed by agitation, a cell suspension or cell powders are agitated at 50 to 10000 rpm, and preferably 100 to 1000 rpm.

Specific methods for preparation of disrupted products (cells) are as follows. Cells are disrupted by, for example, treating a suspension of a lactic acid bacterium in a known Dyno-Mill cell disruptor (e.g., Dyno-Mill disruptor) using glass beads at a peripheral speed of 10.0 to 20.0 m/s (e.g., about 14.0 m/s) and a treating flow rate of 0.1 to 10 L/10 min (e.g., about 1 L/10 min) at a disruption tank temperature of 10° C. to 30° C. (e.g., about 15° C.) 1 to 7 times (e.g., 3 to 5 times). Alternatively, cells are disrupted by treating a suspension of a lactic acid bacterium with a known wet-type jet-mill cell disruptor (e.g., JN20 Nano Jet Pul) at a discharge pressure of 50 to 1000 Mpa (e.g., 270 Mpa) at a treatment flow rate of 50 to 1000 ml/min (e.g., 300 ml/min) 1 to 30 times (e.g., 10 times). Further, cells can be disrupted by treating lactic acid bacterial cell powder using a known dry-type satellite mill cell disruptor (e.g., GOT5 Galaxy 5) in the presence of any of different balls (e.g., 10-mm zirconia balls, 5-mm zirconia balls, or 1-mm alumina balls) at a rotation speed of 50 to 10,000 rpm (e.g., 190 rpm) for 30 minutes to 20 hours (e.g., 5 hours). Cells can also be disrupted by treating lactic acid bacterial cell powder using a known dry-type jet-mill cell disruptor (e.g., Jet-O-Mizer) at a feeding speed of 0.01 to 10000 g/min (e.g., 0.5 g/min) and a discharge pressure of 1 to 1,000 $kg/cm^2$ (e.g., 6 $kg/cm^2$) 1 to 10 times (e.g., once).

According to the present invention, although the disrupted cells of a lactic acid bacterium exhibit the above-described effect even when the cells are merely perforated, it is preferable to prepare the disrupted cells so that the average long diameter or surface area of each cell of a lactic acid bacterium is 90% or less of that before disruption treatment. When cells are disrupted via lysis treatment, for example, the average long diameter or surface area of the cells may be close to 0%. As such, a lactic acid bacterium may be disrupted so that the average long diameter or surface area of disrupted cells is 90% or less, preferably 80% or less, more preferably 70% or less, further preferably 20% to 70% or less, and still further preferably 10% to 50% or less of that before disruption.

Lactic acid bacteria to be subjected to disruption are preferably almost completely disrupted (specifically, 90% or more). However, the substance of the present invention may contain undisrupted lactic acid bacteria accounting for less than about 95%, less than about 90%, less than about 80%, less than about 70% or less than about 60%, preferably less than about 50% or less than about 40%, and further preferably less than about 30%, 20%, 10%, or 5%, as long as the effect of improving arthritis is significant (p<005, preferably p<0.03) compared with that of the lactic acid bacteria before disruption. For example, in the case of wet-type jet mill, undisrupted lactic acid bacteria account for almost 0% and in the case of dry-type jet mill, undisrupted lactic acid bacteria account for about 80% to about 90%.

Desirably, intact lactic acid bacterial cells and/or disrupted cells may be further treated. Examples of such treatment are described below.

Intact lactic acid bacterial cells and/or disrupted cells thereof can be prepared in the form of a suspension or diluted solution by suspending or diluting the cells in an adequate solvent. Examples of a solvent that can be used include water, physiological saline, and phosphate buffered saline (PBS).

The intact lactic acid bacterial cells and/or disrupted cells thereof can be treated by sterilization to prepare a sterilized product. Such intact lactic acid bacterial cells and/or disrupted cells can be sterilized by a known sterilization technique, such as filtration sterilization, radiation sterilization, overheat sterilization, or pressure sterilization.

Alternatively, the intact lactic acid bacterial cells and/or disrupted cells thereof can be treated by heating to prepare a heated product. To prepare such heated product, intact lactic acid bacterial cells and/or disrupted cells thereof are subjected to high-temperature treatment at an elevated temperature (e.g., at 80° C. to 150° C.) for a predetermined period of time, for example, about 10 minutes to 1 hour (e.g., about 10 to 20 minutes).

Further, disrupted cells of a lactic acid bacterium (a portion of cells may be mixed therein) can be processed into the form of powder or granules via drying. Examples of specific drying methods include, but are not particularly limited to, spray dry, drum dry, hot air dry, vacuum dry, and lyophilization, which can be used alone or in combination. Upon drying, excipients that are conventionally used may be added as necessary.

Further, an ingredient or fraction having the effect of improving arthritis may be purified from disrupted cells of a lactic acid bacterium by a known separation or purification method. Thus, such an ingredient can be identified. Examples of such method for separation and/or purification include: a method utilizing solubility, such as salt precipitation or organic solvent precipitation; a method utilizing a difference in molecular weight, such as dialysis, ultrafiltration, or gel filtration; a method utilizing a difference in charge, such as ion-exchange chromatography; a method utilizing specific affinity, such as affinity chromatography; and a method utilizing hydrophobicity, such as hydrophobic chromatography or reverse phase chromatography. These methods can be used alone or in combinations of two or more methods. The thus purified ingredients or fractions having the effect of improving arthritis may be contained in the substance of the present invention comprising disrupted cells of an anti-inflammatory lactic acid bacterium.

2. Composition

The above substance of the present invention, which is obtained by the above techniques and has the effect of preventing or improving arthritis, can be alone formed into or formed with other ingredients into a composition (which can also be referred to as "additive" or "additive agent") for preventing or improving arthritis.

Such a composition can be added to a product such as a food or drink, a feedstuff, or a medicament.

Nonconsecutive intake of the substance or the composition of the present invention is expected to lead to the effect of preventing or improving arthritis, or the effect of preventing or improving diseases or disorders associated with arthritis.

The substance of the present invention for preventing and/or improving arthritis contains as active ingredients the above-mentioned disrupted cells of an anti-inflammatory lactic acid bacterium. The substance may contain disrupted cells of one type of lactic acid bacterium, disrupted cells of multiple different lactic acid bacteria, or may further contain a combination of disrupted cells of multiple different lactic acid bacteria obtained by different disruption treatments.

Furthermore, in addition to disrupted cells of a lactic acid bacterium as an active ingredient, one of or a combination of additives described later, other existing (known) substances having an anti-inflammatory effect, such as a joint-function protecting material, and the like may be added to the composition of the present invention for preventing and/or improving arthritis, as long as the effect of interest is enhanced.

Examples of an existing substance having an anti-inflammatory effect include, but are not limited to, collagen, glucosamine, chondroitin, ω3 fatty acid (e.g., eicosapentaenoic acid (EPA) and docosahexaenoic acid (DHA)), conjugated fatty acids (e.g., conjugated linoleic acid (CLA)), amino acids (e.g., serine and threonine), and salts thereof.

The term "salt" as used herein refers to a salt with organic or inorganic acid or base, which is a pharmaceutically acceptable salt. Examples of such a salt include hydrochloride, sulfate, phosphate, sulfonate (e.g., p-toluene sulfonate and methanesulfonate), citrate, oxalate, succinate, ammonium salt, amine salt, alkali metal salt (e.g., sodium salt and potassium salt), and alkaline earth metal salt (e.g., calcium salt and magnesium salt).

According to an embodiment of the present invention, examples of an existing substance having an anti-inflammatory effect include glucosamine, chondroitin, salts thereof, or a combination thereof.

The dosage form of the product containing the substance or the composition of the present invention, such as a medicament and a functional food is not particularly limited. Examples of dosage forms include: oral formulations, such as tablets, capsules, granules, powders, dust formulations, syrups, dry syrups, liquids, suspensions, and inhalers; and enteral formulations such as suppositories. Among them, an oral formulation is preferred. In case of a liquid formulation, such as liquid or suspension, it may be dissolved or suspended in water or a different adequate medium immediately before use. When the product of the present invention is formulated into the form of a tablet or granules, a surface coating may be provided by a well-known method. Further, the composition for improving arthritis of the present invention may be prepared into the dosage form of a controlled-release formulation such as a sustained-release formulation, a delayed-release formulation, or an immediate release formulation with the use of techniques known in the art.

The product for preventing and/or improving arthritis, which is in a dosage form as described above, can be produced according to conventional methods, by formulating generally used additives, such as excipients, disintegrators, binders, wetting agents, stabilizers, buffers, lubricants, preservatives, surfactants, sweeteners, corrigents, aromatics, acidulants, and coloring agents, into the ingredients as described above, depending on types of dosage forms.

Where the composition of the present invention is prepared into a medicament, for example, pharmaceutically acceptable carriers or additives can be formulated into the composition of the present invention. Examples of the pharmaceutically acceptable carriers and additives include water, pharmaceutically acceptable organic solvents, collagen, polyvinyl alcohol, polyvinyl pyrrolidone, carboxyvinyl polymers, sodium alginate, water-soluble dextran, water-soluble dextrin, sodium carboxymethyl starch, pectin, xanthan gum, gum arabic, casein, gelatin, agar, glycerin, propylene glycol, polyethylene glycol, vaseline, paraffin, stearyl alcohol, stearic acid, human serum albumin, mannitol, sorbitol, lactose, surfactants acceptable as pharmaceutical additives, and artificial cell constructs such as liposomes.

Where the composition of the present invention contains the above-described additives, other inflammation improving materials or the like, the content of disrupted cells of a lactic acid bacterium used as active ingredients varies depending on dosage forms. The amount of lactic acid bacterial cells before disruption treatment is generally 0.0001% to 99% by mass, preferably 0.001% to 80% by mass, and more preferably 0.001% to 75% by mass. It is preferable that the composition be prepared into a dosage form that allows management of the daily dose, so that a preferable amount of the active ingredient can be taken. In addition, disrupted cells of a lactic acid bacterium are contained in the composition of the present invention in an amount of approximately $10^7$ cells/g to approximately $10^{12}$ cells/g, and preferably approximately $10^8$ cells/g to approximately $10^{12}$ cells/g, when counted as the number of lactic acid bacterial cells before disruption.

Examples of other arthritis improving materials that can be added to or incorporated into the composition of the present invention include, but are not limited to, materials for improving joint functions (e.g., hyaluronic acid, collagen, glucosamine, chondroitin, and a salt thereof) and anti-inflammatory fatty acid (e.g., DHA, EPA, and CLA)). In addition, the ratio of the ingredients is preferably basically 2 to 9 parts by weight of disrupted cells (e.g., 3 parts by weight) to 1 part by weight. The ratio thereof may be varied depending on conditions.

Furthermore, for the production of medicaments, foods or drinks, or feedstuffs, the substance or the composition of the present invention may be mixed with various additives or other various substances, which are generally used for production thereof.

Examples of such substances and additives include, but are not limited to, a variety of fats and oils (e.g., plant oils, such as soybean oil, corn oil, safflower oil, and olive oil, and animal fats and oils, such as beef fat and sardine oil), crude drugs (e.g., royal jelly and ginseng), amino acids (e.g., glutamine, cysteine, leucine, and arginine), polyalcohols (e.g., ethylene glycol, polyethylene glycol, propylene glycol, glycerin, and sugar alcohols such as sorbitol, erythritol, xylitol, maltitol, and mannitol), natural polymers (e.g., gum arabic, agar, water-soluble corn fibers, gelatin, xanthan gum, casein, gluten or gluten hydrolysate, lecithin, starch, and dextrin), vitamins (e.g., vitamin C and B-complex vitamins), minerals (e.g., calcium, magnesium, zinc, and iron), dietary fibers (e.g., mannan, pectin, and hemicellulose), surfactants (e.g., glycerin fatty acid esters and sorbitan fatty acid esters), purified water, excipients (e.g., glucose, cornstarch, lactose, and dextrin), stabilizers, pH-adjusting agents, antioxidants, sweeteners, taste components, acidulants, coloring agents, and flavors.

One or more types of ingredients or additives can be incorporated into the substance or the composition of the present invention for production of foods or drinks or feedstuffs. Specific examples thereof include functional ingredients or additives, such as various organic acids, flavonoids, polyphenols, catechins, xanthine derivatives, nondigestible oligosaccharides such as fructooligosaccharide, polyvinylpyrrolidone, anti-inflammatory peptides, and animal feedstuffs.

The amount of such ingredient or additive can be adequately determined depending on the type of additive and the desirable intake. The content of disrupted cells of a lactic acid bacterium used as active ingredients varies depending on the dosage form. The content is desirably generally 0.0001% to 99% by mass, preferably 0.001% to 80% by mass, and more preferably 0.001% to 75% by mass, as the amount of the lactic acid bacterium before disruption treatment.

Subjects of administration or intake of the substance or the composition of the present invention are vertebrate animals. Specific examples thereof include mammals such as humans, primates (e.g., monkeys and chimpanzees), livestock animals (e.g., cattle, horses, pigs, sheep, and chickens), pet animals (e.g., dogs and cats), experimental animals (e.g., mice and rats), animals for competition (e.g., racehorses), and others including reptiles and birds (e.g., chickens). Particularly preferable subjects are humans who are suspected of having articular inflammation, humans who have already developed arthritis, humans who have damaged joints, humans who are at a high risk of developing abnormal immune functions such as an autoimmune disease due to genetic or environmental factors, or humans who had suffered or are suffered from such abnormality or disease in the past or present. Preferable examples of such an autoimmune disease include rheumatoid arthritis and collagen disease.

The dose of administration or intake of a medicament or a functional food or drink containing the substance or the composition of the present invention varies depending on the age and body weight of a subject, the number of doses for administration/intake, the severity of symptoms, and other conditions. The dose can be changed extensively at the discretion of a practitioner to achieve a desired effect. For oral administration or intake, for example, it is preferable to administer or take disrupted cells of a lactic acid bacterium contained in the medicament or the functional food or drink in an amount of generally approximately $10^6$ cells to $10^{12}$ cells, and preferably approximately $10^7$ cells to $10^{11}$ cells per kg of body weight (of a subject), as the amount of the lactic acid bacterium before disruption treatment. The content of disrupted cells of a lactic acid bacterium is not particularly limited and can be adequately adjusted in accordance with the ease of production, the preferable daily dose, or other conditions of a product to be produced herein. Since the substance for preventing and/or improving arthritis of the present invention is highly safe, it is also possible to further increase the dose to be administered or taken. A daily dose may be administered or taken in a single dosage, or it may be administered or taken in several separate dosages. In addition, the frequency of administration or intake is not particularly limited, and it can be adequately selected depending on various conditions, such as route of administration or intake, age or body weight of a subject, severity of arthritis, presence or absence of onset of a disease or disorder caused by arthritis, and desired effects (e.g., therapeutic or preventive effects).

The administration or intake route of a product such as a medicament or a functional food or drink containing the substance or the composition of the present invention can be, for example, oral administration or intake, or parenteral administration such as rectal administration. Particularly preferably, such product of the present invention is orally administered or taken.

The substance or the composition of the present invention has an effect of preventing and improving a disease or a disorder associated with articular inflammation in a subject. Specifically, the substance or the composition of the present invention has an effect of alleviating articular inflammatory disease by decreasing the levels of an inflammatory cytokine, a synovial membrane growth factor, and an inflammation mediator and/or elevating the level of an inhibitory cytokine in a subject. Therefore, the substance or the composition having the effect of preventing and/or improving arthritis of the present invention exhibits excellent preventive, improvable or ameliorative, and therapeutic effects on diseases or disorders associated with articular inflammation. In addition, such substance or composition is highly safe, and it can be continuously administered or taken for a long period of time. As such, the composition of the present invention can also be used as a food or drink or a feedstuff.

As described above, the substance or the composition of the present invention exhibiting the effect of preventing and/or improving arthritis can be used not only for prevention or treatment of a disease or a disorder associated with articular inflammation, in the form of a functional food or drink or a functional feedstuff supplemented therewith, but also for use as a medicament supplemented with the substance or the composition of the present invention.

The term "disease(s) or disorder(s) associated with articular inflammation" as used herein refers to diseases, disorders, symptoms or syndrome of joints due to immunopotentiation. Examples of such disease or disorder associated with articular inflammation include, but are not limited to, osteoarthritis (e.g., knee osteoarthritis), rheumatoid arthritis, tenosynonitis, periomarthritis, tendinitis, coxitis, and locomotive syndrome.

In the present invention, the term "prevention or treatment" of diseases or disorders associated with articular inflammation refers to prevention of the onset of diseases or disorders associated with articular inflammation or treatment of the developed diseases or disorders associated with articular inflammation (i.e., the disease state) of a subject such as an animal or a human. The term also refers to delay or suppression of the onset of diseases or disorders associated with articular inflammation. Further, this term refers to prevention of the onset of diseases or disorders resulting from diseases or disorders associated with articular inflammation. When a product containing the substance or the composition having the effect of preventing and/or improving arthritis of the present invention is used for a preventive purpose, for example, it is preferable that the substance or the composition be administered to or taken by subjects having genetic factors, environmental factors, or other abnormalities that may cause diseases or disorders associated with articular inflammation, or subjects who had developed diseases or disorders associated with articular inflammation in the past.

The target disease or disorder associated with articular inflammation to be treated or prevented with the aid of the above-mentioned product containing the substance or the composition of the present invention may be a single or combined diseases or disorders, or may be combined with a disease other than those mentioned above.

The medicament for preventing and/or improving arthritis of the present invention may be used in combination with another medicament or another therapeutic or preventive method. The "other medicament" and the composition for improving arthritis of the present invention may be formulated into a single formulation. Alternatively, they may be formulated into separate formulations to administer them simultaneously or at intervals.

As described above, a food or a feedstuff for preventing and/or improving arthritis, containing the substance or the composition of the present invention has an effect of improving arthritis. In addition, such food or feedstuff comprises substances produced by lactic acid bacteria, which have been conventionally used for meals, and thus is highly safe. Even when it is added to a variety of foods or drinks, or feedstuffs further, it does not inhibit the flavor thereof. Thus, it can be added to a variety of foods or drinks or feedstuffs and can be continuously taken by a subject. This is expected to prevent or ameliorate arthritis in the subject.

The food or drink of the present invention comprises a substance that contains as active ingredients the above-mentioned disrupted cells of a lactic acid bacterium having the effect of preventing or improving arthritis. In the present invention, the term "food(s) or drink(s)" refers to both beverages and foods. Examples of the food or drink comprising the substance or the composition of the present invention include all foods or drinks into which the substance or the composition of the present invention having the effect of preventing and/or improving arthritis can be incorporated, in addition to foods or drinks such as health foods or drinks for promotion of health with the use of the effect of improving arthritis, functional foods or drinks, and foods or drinks for specified health use.

Functional foods or drinks are particularly preferable as foods or drinks containing the substance of the present invention. The term "functional foods or drinks" as used herein means foods or drinks having predetermined functionality for organisms and encompasses, for example, all of so-called general health foods or drinks such as foods or drinks with health claims including foods for specified health use (including qualified FOSHU [food for specified health use]) and foods or drinks with nutrient function claims, foods or drinks for special dietary uses, nutritional supplements, health supplements, supplements (e.g., those having a variety of dosage forms such as tablets, coated tablets, sugar-coated tablets, capsules, and liquid agents), and beauty foods or drinks (e.g., diet foods or drinks). The functional foods or drinks of the present invention also encompass health foods or drinks to which health claims based on Codex (Joint FAO/WHO Food Standards Programme) food standards are applied.

Specific examples of foods or drinks include: liquid diets such as tube enteral nutritional supplements; health foods or drinks in dosage forms such as tablet candies, tablets, chewable tablets, tablets, dust formulations, powders, capsules, granules, and tonic drinks, and nutritional supplements; beverages such as tea beverages (e.g., green tea, oolong tea, and black tea), soft drinks, jelly beverages, isotonic beverages, milk beverages, carbonated beverages, vegetable beverages, juice beverages, fermented vegetable beverages, fermented juice beverages, fermented milk beverages (e.g., yogurt), lactic acid beverages, milk beverages (e.g., coffee milk and fruit milk), beverages containing drink powders, cocoa beverages, milk, and purified water; spreads such as butter, jam, dried seasoning products, and margarine; mayonnaise, shortening, custard, dressings, bread, boiled rice, noodles, pasta, miso soup, tofu, yogurt, soup, sauces, and sweets (e.g., biscuits or cookies, chocolate, candies, cake, ice cream, chewing gum, and tablets).

The food or drink of the present invention can be produced according to conventional methods by adding other food materials used for production of the above-mentioned foods or drinks, such as various nutrients, various vitamins, minerals, dietary fibers, and various additives (e.g., taste components, sweeteners, acidulants such as organic acids, stabilizers, and flavors), in addition to the above-mentioned substance or composition of the present invention.

For the food or drink of the present invention, persons skilled in the art can adequately determine the amount of the substance of the present invention formulated in consideration of the form of the food or drink and the taste or texture that are required. In the substance of the present invention to be added, the above anti-inflammatory lactic acid bacterium that is not disrupted can be contained to account for about less than 95%, less than about 90%, less than about 80%, less than about 70%, less than about 60%, preferably less than about 50% or less than about 40%, and further preferably less than about 30%, less than about 20%, less than about 10%, less than about 5% or less than about 2% of the bacterial cell count before disruption.

The substance of the present invention is highly safe and thus the amount thereof to be incorporated into a food or drink can further be increased. It is preferable that the food or drink be prepared into a dosage form that allows management of the daily dose, so as to enable drinking or eating of a preferable intake of the substance. As such, the food or drink of the present invention can be taken via drinking or eating that allows management of preferable dose of the substance of the present invention. Thus, a method for preventing and a method for improving diseases or disorders associated with arthritis using the food or drink are provided.

The substance or the composition of the present invention may be incorporated into a food or drink by an arbitrary appropriate method available to persons skilled in the art. For example, the substance or the composition of the present invention can be prepared in a form of liquid, gel, solid, powder, or granules and then incorporated into foods or drinks. Alternatively, the substance or the composition of the present invention may be mixed or dissolved directly into raw materials for foods or drinks. The substance or the composition of the present invention may be applied to, coated onto, infiltrated into, or sprayed onto foods or drinks. The substance or the composition of the present invention may be dispersed uniformly or distributed unevenly in foods or drinks. A capsule or the like containing the substance or the composition of the present invention may be prepared. An edible film or food coating agent may be wrapped around the substance or the composition of the present invention. Alternatively, the substance or the composition of the present invention may be prepared into a form such as tablet after the addition of an appropriate excipient or the like thereto. The food or drink comprising the substance or the composition of the present invention may further be processed. Such a processed product also falls within the scope of the present invention.

In the production of the food or drink of the present invention, a variety of additives routinely used in foods or drinks may be employed. Examples of the additives include, but are not limited to, color formers (e.g., sodium nitrite), coloring agents (e.g., gardenia pigments and Red 102), flavors (e.g., orange flavors), sweeteners (e.g., stevia and aspartame), preservatives (e.g., sodium acetate and sorbic acid), emulsifiers (e.g., sodium chondroitin sulfate and propylene glycol fatty acid ester), antioxidants (e.g., disodium EDTA and vitamin C), pH adjusting agents (e.g., citric acid), chemical seasonings (e.g., sodium inosinate), thickeners (e.g., xanthan gum), swelling agents (e.g., calcium carbonate), antifoaming agents (e.g., calcium phosphate), binders (e.g., sodium polyphosphate), nutrition-enriching agents (e.g., calcium-enriching agents and vitamin A), and excipients (e.g., water-soluble dextrin). Functional raw materials such as Panax ginseng extracts, Acanthopanax senticosus Harms extracts, eucalyptus extracts, or du zhong tea extracts may further be added.

As described above, the food or drink of the present invention has the effect of preventing and/or improving arthritis. As such, it exhibits an excellent effect of preventing or improving diseases or disorders associated with articular inflammation. In addition, it is highly safe, and thus there is no concern about side effects. Further, when the substance of the present invention is added to various foods or drinks, it does not inhibit the flavor thereof. Accordingly, the so obtained foods or drinks can be easily used for long-term continuous intake. Thus, the effect of preventing and improving diseases or disorders associated with articular inflammation will be able to be expected.

Furthermore, the substance or the composition of the present invention can be formulated not only into foods or drinks for humans but also into feedstuffs for animals such as livestock, racehorses, and pets as described above. Feedstuffs are substantially equivalent to foods or drinks except that they are given to non-human subjects. Therefore, the above descriptions of foods or drinks can also be applied to feedstuffs.

EXAMPLES

The present invention will hereafter be described in greater detail with reference to the following examples, although the technical scope of the present invention is not limited thereto.

Example 1

Lactic acid bacteria, the *Lactobacillus amylovorus* CP1563 strain (FERM BP-11255), the *Lactobacillus gasseri* CP2305 strain (FERM BP-11331), and the *Lactobacillus acidophilus* CL-92 strain (FERM BP-4981), were as prepared as follows.

The *Lactobacillus amylovorus* CP1563 strain, the *Lactobacillus gasseri* CP2305 strain, and the *Lactobacillus acidophilus* CL-92 strain were sampled and isolated from human feces. These strains were identified based on 16S rDNA nucleotide sequence analysis and phenotype observation.

These strains were deposited under Accession Numbers FERM BP-11255, FERM BP-11331, and FERM BP-4981, with the International Patent Organism Depositary, the National Institute of Advanced Industrial Science and Technology (AIST) (Tsukuba Central 6, 1-1-1 Higashi, Tsukuba, Ibaraki, 305-8566, Japan).

The lactic acid bacteria were each cultured using a homemade, food-grade medium for lactic acid bacteria at 37° C. for 18 hours and then collected via centrifugation. The bacterial strains were each washed with deionized water, harvested, resuspended in an adequate amount of water, and sterilized at a temperature of 90° C. The sterilized suspension was subjected to disruption using Dyno-Mill under conditions as described below.

Apparatus used: Dyno-Mill disruptor (Multi-Lab 0.6 L, Shinmaru Enterprises Corporation)
Peripheral speed: 14.0 m/s
Treatment flow rate: 1 L/10 min
Number of treatments: 5 times
Disruption tank temperature: 15° C.
Glass beads used: diameter 0.5 mm, 0.4 L As a result of disruption treatment, the average long diameter of cells in each suspension of lactic acid bacterium was reduced to 68% of that before treatment (i.e., 2.77 µm→1.89 µm). FIG. 1A and FIG. 1B show the photomicrographs of cells before disruption treatment and those after disruption treatment. As shown in FIG. 1B, completely disrupted cells were obtained by disruption treatment. After disruption, the suspension was lyophilized, and a lyophilized powder of the disrupted lactic acid bacterium was obtained. When the cells were not disrupted (A; intact (control)), the sterilized solution as such was lyophilized, and a lyophilized powder of the undisrupted lactic acid bacterium was obtained. The intact cells accounted for 99.99% or more of the lyophilized powder used as a control.

Example 2

As described below, the lyophilized powder of the undisrupted lactic acid bacterium was examined for the effect of preventing the onset of rat adjuvant arthritis. Regarding these test substances, the lyophilized powder of each undisrupted lactic acid bacterium was continuously administered via dietary administration during a period ranging from the day 2 weeks before sensitization with an adjuvant to day 21 (at the end of the test (3% (w/w)).

<Test Substance and Method for Preparing the Same>

Various lactic acid bacteria were prepared as described above and then lyophilized by a conventional method, each of which was subsequently mixed into a commercially available MF feedstuff (Oriental Yeast Co., ltd.). Then, the rats were fed ad libitum with the feedstuff. Glucosamine (Miyako Kagaku Co., Ltd.) and chondroitin (Maruha Nichiro Foods, Inc.) were mixed with feedstuffs to account for 1% of the weight of such feedstuff, and then rats were fed ad libitum therewith.

<Preparation of Adjuvant>

Freund's complete adjuvant (FCA) to be used for sensitization was prepared by weighing an appropriate amount of M. tuberculosis H37Ra (Wako Pure Chemical Industries, Ltd.), pulverizing it with an agate mortar, gradually adding liquid paraffin (Wako Pure Chemical Industries, Ltd.) for suspension, and thus preparing a suspension (6 mg/ml). Preparation was carried out on the day of sensitization with the adjuvant.

<Experimental Animals>

Wistar female rats (SPF) (8-week-old) purchased from Japan SLC Inc. were preliminary raised for 14 days and then subjected to the experiment. Rats were raised in a room (time for lighting: 8 to 18 hours) for raising rats at room temperature of 24±3° C. and relative humidity of 55±15% throughout the preliminary raising period and experiment period.

Rats (2 to 3 animals/cage) of all groups were fed ad libitum with solid feedstuffs (MF, Oriental Yeast Co., ltd.) and sterile deionized water.

<Induction of Arthritis>

Each rat was fixed under isoflurane anesthesia on a fixation base, and then 0.1 ml of the prepared adjuvant was injected intradermally into a footpad of the right hind leg to induce arthritis. In addition, the day on which arthritis was induced was designated as day 0.

<Route of Administration and Group Composition>

Administration method: ad libitum feeding with 3% in diet
Administration period: day 14 to day 21
Number of animals: 10 animals/group <Group Composition>

TABLE 1

| | Lactic acid bacteria tested | | |
|---|---|---|---|
| Group No. | Name of group | Lactic acid bacterium mixed in feed (%) | Number of animals |
| 1 | Placebo (base feed alone) | 0 | 10 |
| 2 | L. acidophilus CL-92 | 3 | 10 |
| 3 | L. amylovorus CP1563 | 3 | 10 |
| 4 | L. gasseri CP2305 | 3 | 10 |
| 5 | L. casei SP1 | 3 | 10 |
| 6 | L. rhamnosus SP1 | 3 | 10 |
| 7 | L. paracasei SP1 | 3 | 10 |
| 8 | B. pseudocatenulatum SP1 | 3 | 10 |
| 9 | B. longum SP1 | 3 | 10 |

<Observation and Test Items>

General conditions: Symptoms were observed once a day and the results were entered in a record form.
Body weight: Body weight was measured using a weighing scale on days 0, 5, 9, 14, 19, and 21.
Arthritis score: The degrees of redness, swelling, and tetany of right forelimb, left forelimb, and left hindlimb excluding the right hindlimb (sensitization sites), were subjected to gross observation, and then scored (0 to 4 points) based on the following criteria. Evaluation was made with a maximum score of 12 points. Observation was carried out on days 0, 5, 9, 14, 19, and 21.
  0: nil (no symptoms)
  1: mild (mild symptoms)
  2: moderate (moderate symptoms)
  3: moderately severe (moderately severe symptoms)
  4: severe (severe symptoms)
Foot volume: the volumes of right and left hindlimbs were measured using a foot volume measuring apparatus (MK-101P, Muromachi Kikai Co., Ltd.). Measurement was carried out on the same day as that for observation of arthritis scores.

<Evaluation>

Evaluation results were stable. The degree of the hypertrophy of each sensitized hindlimb, with which parametric analysis was possible, was designated as the primary end point. After repetition of the measurement, data from the final day of intake were compared among groups.

<Statistical Analysis>

The foot volume on day 21 is shown using a box whisker plot. To test the statistical significance for each group, analysis of variance was conducted using SPSS ver12, and differences among groups were detected by a multiple comparison test (Tukey method) for all possible combinations. In cases of $p<0.05$, the results were determined to indicate a significant difference.

<Results and Discussion>
<Sensitized Hind Leg Volume>

Figure 2:
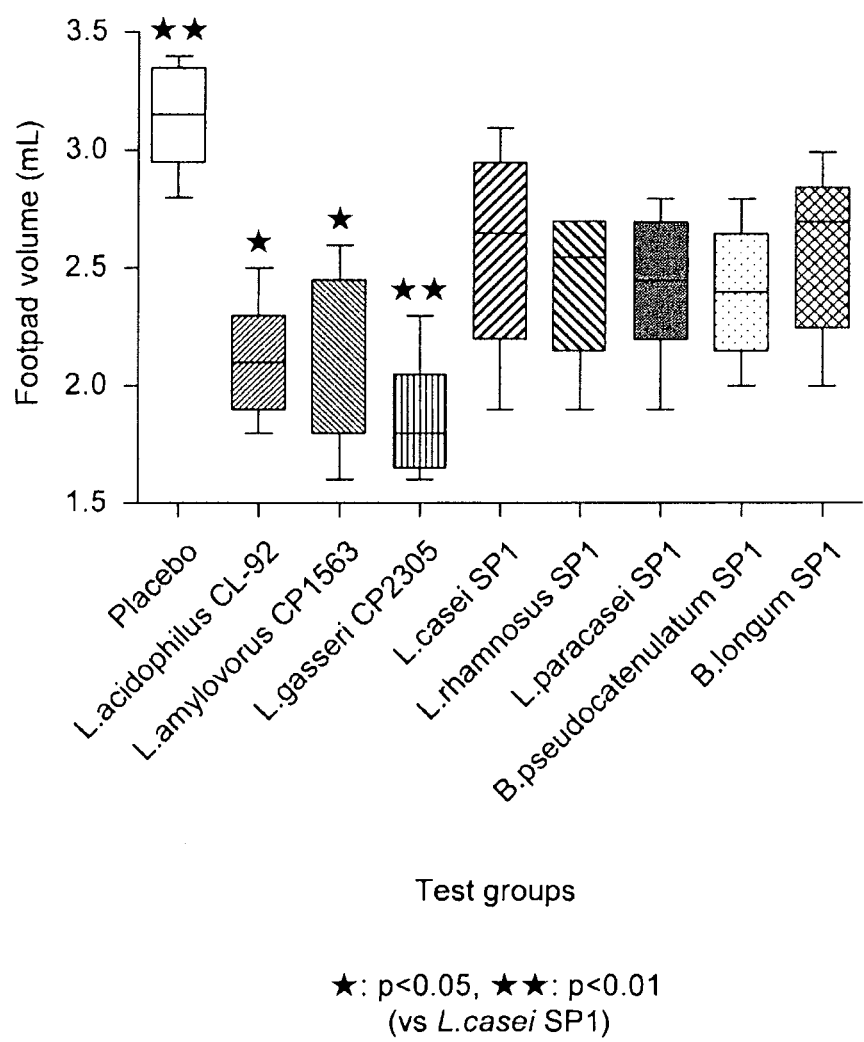
FIG. 2 is a graph showing differences in the inflammation-suppressing effect of different lactic acid bacteria showing anti-inflammatory effect in an adjuvant-induced arthritis rat model. The inflammation-suppressing effect was evaluated using a decrease in footpad thickness of rat left and right hindlimbs as an indicator.

FIG. 2 shows the result of measuring the volume of a sensitized hindlimb (right hindlimb) on day 21, as an example. This is an example of the result of comparison and examination of the lyophilized powder of the undisrupted lactic acid bacterium for the effect of preventing the onset of rat adjuvant arthritis.

All strains of lactic acid bacteria administered significantly suppressed the sensitized hindlimb (right hindlimb) volumes. Although the effect of suppressing arthritis was obtained in all cases, there were differences in efficiency. In particular, the *Lactobacillus gasseri* CP2305 strain, the *Lactobacillus amylovorus* CP1563 strain, and the *Lactobacillus acidophilus* CL-92 strain were revealed to have high effects of improving the disease. It was thus verified that the desirable effect of improving arthritis can be obtained by selecting lactic acid bacteria (including bacteria of these strains) having a high anti-inflammatory effect.

Example 3

Figure 3:
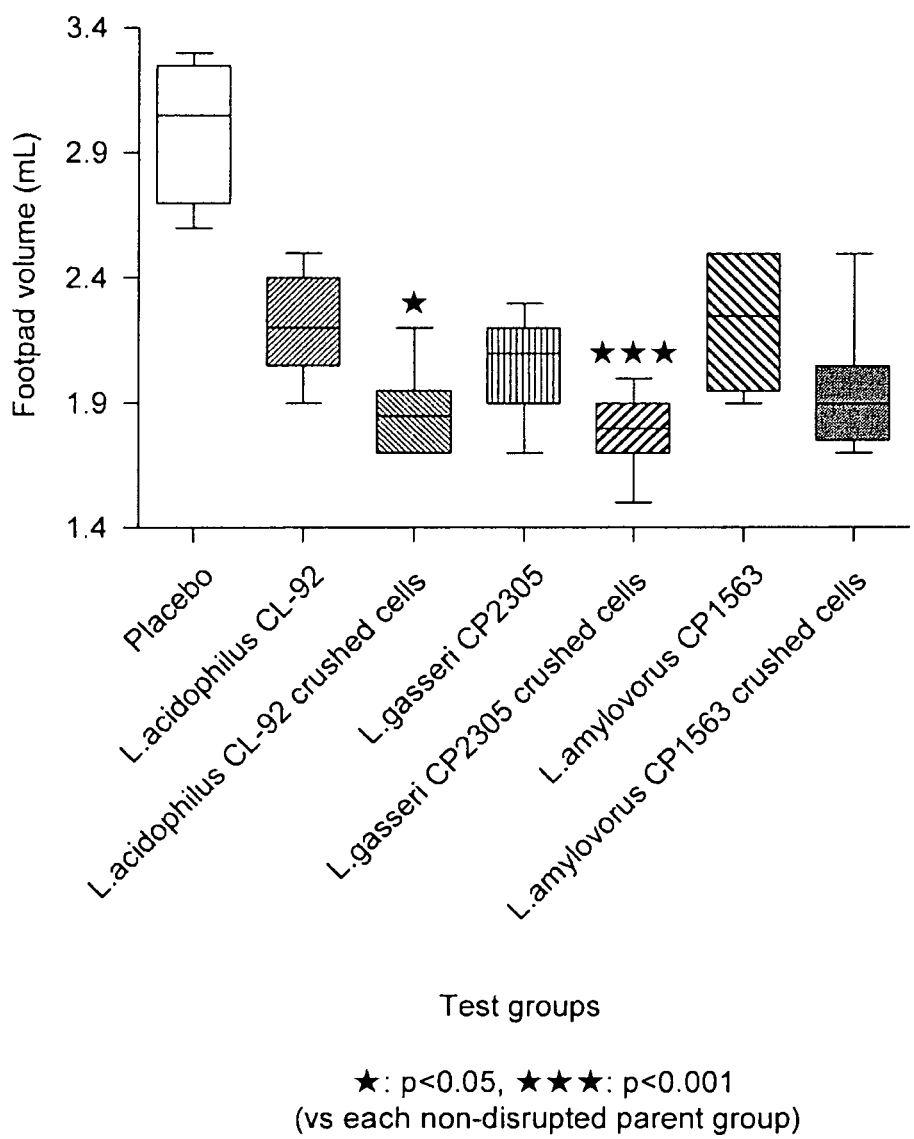
FIG. 3 is a graph showing the inflammation-suppressing effect enhanced by disruption of different lactic acid bacteria showing anti-inflammatory effect in an adjuvant-induced arthritis rat model. Disrupted cells are indicated as "crushed." The inflammation-suppressing effect was evaluated using a decrease in footpad thickness of rat left and right hindlimbs as an indicator.

In this example, an example is described, in which the effect of disrupting lactic acid bacteria to be administered to an adjuvant arthritis rat were verified. Cases in which the disrupted cells of the *Lactobacillus acidophilus* CL-92 strain, the *Lactobacillus gasseri* CP2305 strain, and the *Lactobacillus amylovorus* CP1563 strain (prepared by the method for disrupting cells as described in Example 1) had been administered were compared with cases in which undisrupted cells thereof had been administered (FIG. 3).

In the cases of the *Lactobacillus acidophilus* CL-92 strain and the *Lactobacillus gasseri* CP2305 strain, significant differences were observed between disrupted cells and undisrupted cells (p<0.05), indicating that disruption treatment is effective.

Example 4

Figure 4:
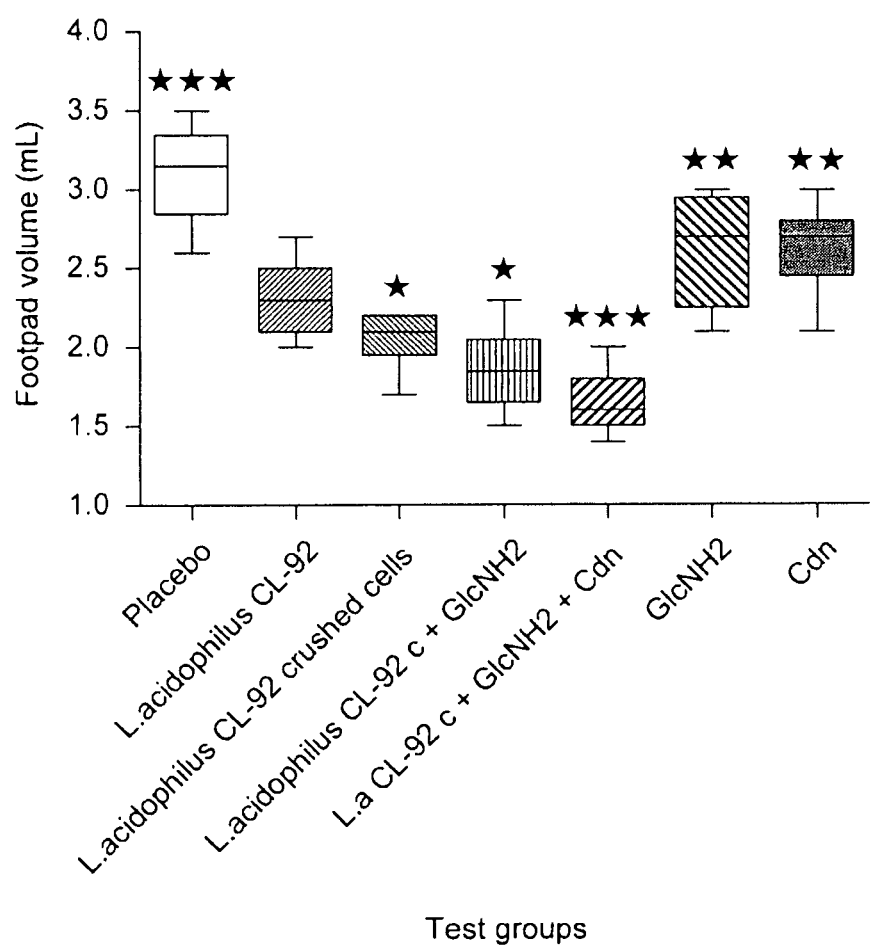
FIG. 4 is a graph showing the synergistic inflammation-suppressing effect of the disrupted cells (crushed) of *Lactobacillus acidophilus* CL-92 strain and known joint protecting materials (glucosamine (GlcNH2) and/or chondroitin (Cdn)) in an adjuvant-induced arthritis rat model. The inflammation-suppressing effect was evaluated using a decrease in footpad thickness of rat left and right hindlimbs as an indicator.
Figure 5:
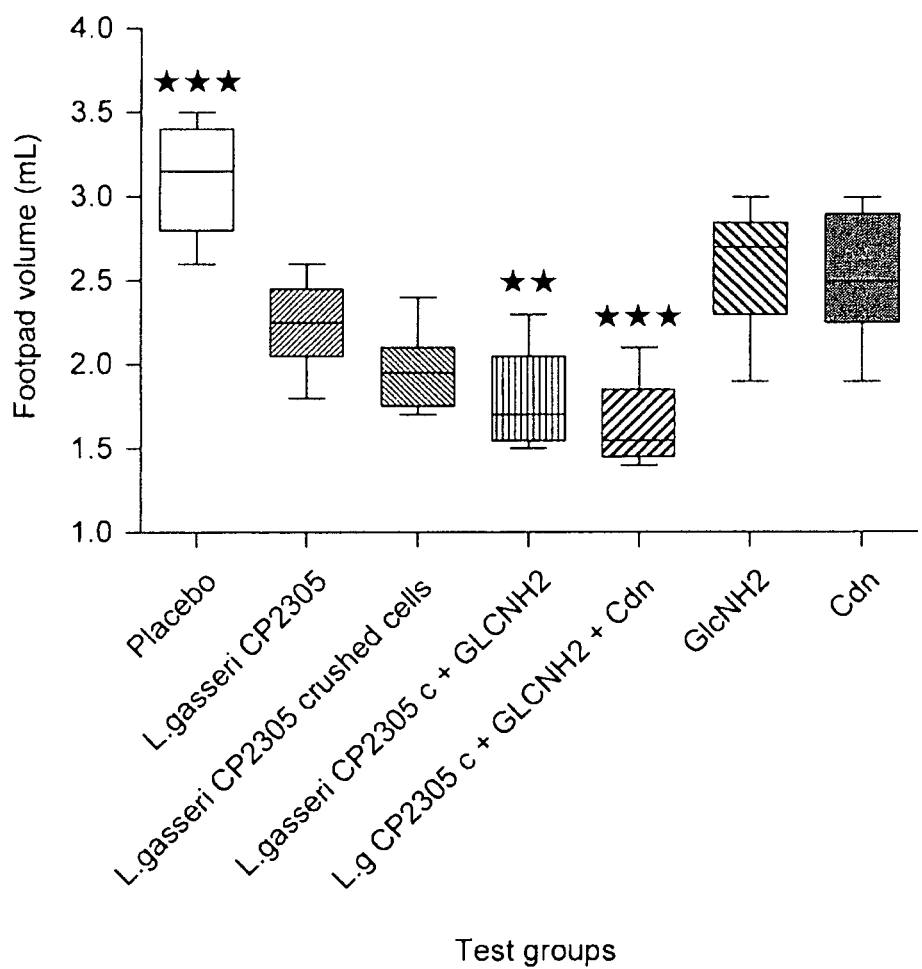
FIG. 5 is a graph showing the synergistic inflammation-suppressing effect of the disrupted cells (crashed) of *Lactobacillus gasseri* CP2305 strain and known joint protecting materials (glucosamine (GlcNH2) and/or chondroitin (Cdn)) in an adjuvant-induced arthritis rat model.

In this example, the synergistic effect (positive interaction) of disrupted lactic acid bacteria and glucosamine (GlnNH2) or glucosamine (GlnNH2)+chondroitin (Cdn) to be administered to adjuvant arthritis rats is described using the *Lactobacillus acidophilus* CL-92 strain (Experiment 1: FIG. 4) and the *Lactobacillus gasseri* CP2305 strain (Experiment 2: FIG. 5) as examples.

In the case of examination of the *Lactobacillus acidophilus* CL-92 strain, clear interaction was obtained with the addition of other materials. Moreover, disrupted cells of the *Lactobacillus acidophilus* CL-92 strain exhibited a high contribution to the effect of improving arthritis, and glucosamine and chondroitin were found to have the effect of enhancing the above effect.

Meanwhile, results completely similar to the above were obtained for the *Lactobacillus gasseri* CP2305 strain. The absolute effect thereof was found to be equivalent to or stronger than that of the *Lactobacillus acidophilus* CL-92 strain.

Example 5

<Verification of the Effect of Anti-Inflammatory Lactic Acid Bacterium on Rheumatoid Arthritis>

With the use of IL-1Ra KO female mice (6-week-old) reproduced at the Graduate School of Agricultural and Life Sciences, the University of Tokyo (Tokyo, Japan) as rheumatoid arthritis model mice, the *Lactobacillus acidophilus* CL-92 strain (the lyophilized powder thereof having exhibited a high effect of preventing the onset of rat adjuvant arthritis) was verified regarding the effect for improving rheumatoid arthritis, as described below, for example. In this example, cells (undisrupted) of anti-inflammatory lactic acid bacteria (confirmed to have the effect of disrupting lactic acid bacteria in Examples 3 and 4) were used. When disrupted cells are used, it is clear that the resulting inflammation-suppressing effect is better than that of a case in which cells are directly used. In view of the results shown in FIG. 3, it is also clear that the effect of improving rheumatoid arthritis can be obtained with the use of the *Lactobacillus gasseri* CP2305 strain, the *Lactobacillus amylovorus* CP1563 strain, and the disrupted cells thereof. In addition, IL-1Ra KO female mice used in this experiment are known to undergo inflammation as a result of deletion of an endogenous antagonist of the IL-1 receptor, which causes the natural onset of rheumatoid arthritis.

Such an IL-1 receptor antagonist has been developed as a therapeutic agent for rheumatoid arthritis, such as a medicine (e.g., Anakinra)

<Test Substance and Method for Preparing the Same>

Lactic acid bacteria were prepared as described above, and then lyophilized by a conventional method. In a manner similar to that of the experiment for adjuvant arthritis, a commercially available MF feedstuff was mixed with cells (3% in the mixture) (Oriental Yeast Co., ltd), and then mice were fed ad libitum with the feedstuff.

<Experimental Animals>

IL-1Ra KO mice bred at the Graduate School of Agricultural and Life Sciences, the University of Tokyo, were fed with an experimental diet for 19 weeks (6-week-old to 24-week old). Mice were raised in a room (time for lighting: 8 to 18 hours) for raising mice at a room temperature of 24±3° C. and a relative humidity of 55±15% throughout the experimental period.

Mice (5 animals/cage) of all groups were fed ad libitum with an experimental feedstuff and sterile deionized water.

<Group Composition>

TABLE 2

Test groups

| Group No. | Name of group | Lactic acid bacterium mixed in feed (%) | Number of animals |
| --- | --- | --- | --- |
| 1 | Placebo (base feed alone) | 0 | 10 |
| 2 | *L. acidophilus* CL-92 | 3 | 10 |

<Observation and Test Items>

General conditions: Symptoms were observed every week for 19 weeks (6-week-old to 24-week-old) and then the results were entered in a record form.

Arthritis score: The degrees of redness, swelling, and tetany of right forelimb, left forelimb, and left hindlimb excluding right hindlimb (sensitized site) were subjected to gross observation, and then scored (0 to 4 points) based on the following criteria. Evaluation was made with a maximum score of 12 points. Observation was carried out every week for 19 weeks (6-week-old to 24-week-old).

0: nil
1: mild
2: moderate
3: moderately severe
4: severe

Thickening of footpad: Thickness of the footpads of the right and left hindlimbs was measured using a thickness gauge. Measurement was carried out on the same day as that for evaluation of arthritis scores.

<Evaluation>

The average thickness of the footpads of left and right hindlimbs was designated as the primary end point.

<Statistical Analysis>

Differences among groups were compared by repeated measurements analysis of variance (SPSS ver12).

<Results and Discussion>

<Thickness of Sensitized Hindlimb>

Figure 6:
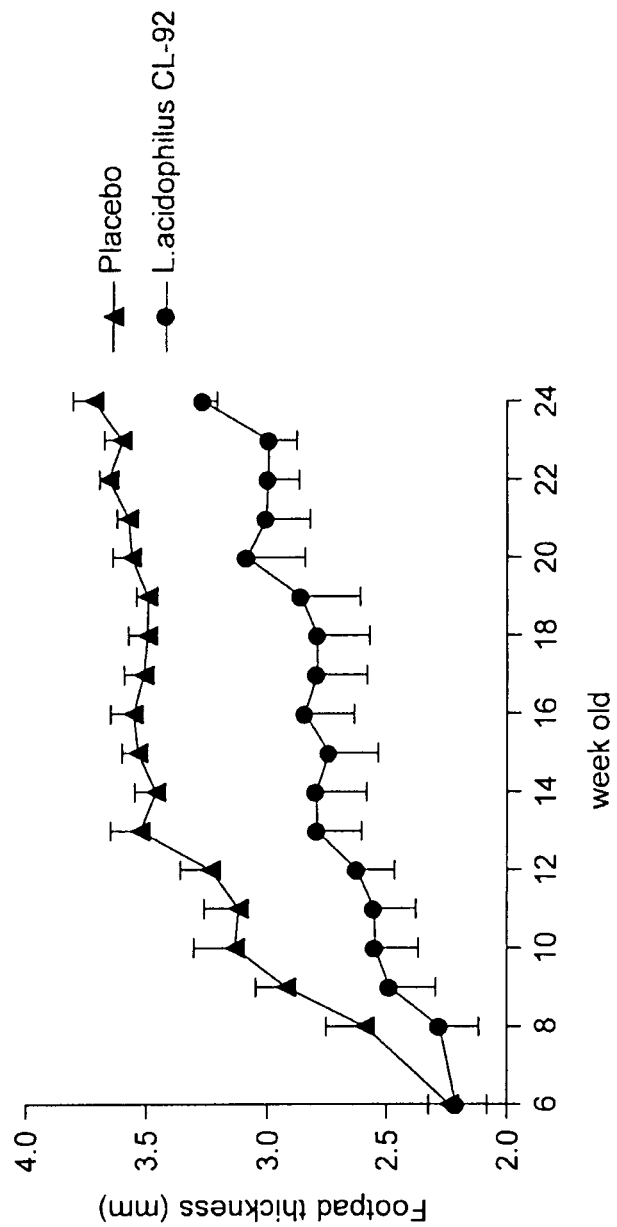
FIG. 6 is a graph showing the inflammation-suppressing effect over time as a result of intake of cells of *Lactobacillus acidophilus* CL-92 strain in a rheumatoid arthritis mouse model. The inflammation-suppressing effect was evaluated using the size of hypertrophy of footpads of rat left and right hindlimbs as an indicator.

FIG. 6 shows the results of measuring the hypertrophy of the footpads of hindlimbs (i.e., average hypertrophy of left and right hindlimbs) during the test period. As a result of examining the lyophilized powder of the *Lactobacillus acidophilus* CL-92 strain for its effect of preventing the onset of rheumatoid arthritis, the *Lactobacillus acidophilus* CL-92 strain administered significantly suppressed (p=0.003) changes in hypertrophy of the footpads of left and right hindlimbs. Thus, the strong effect of suppressing rheumatoid arthritis was obtained. It was verified that the strain also had a high anti-inflammatory effect on rheumatoid arthritis.

<Differences in the Expression of Blood Plasma Cytokines Upon Autopsy>

Figure 7:
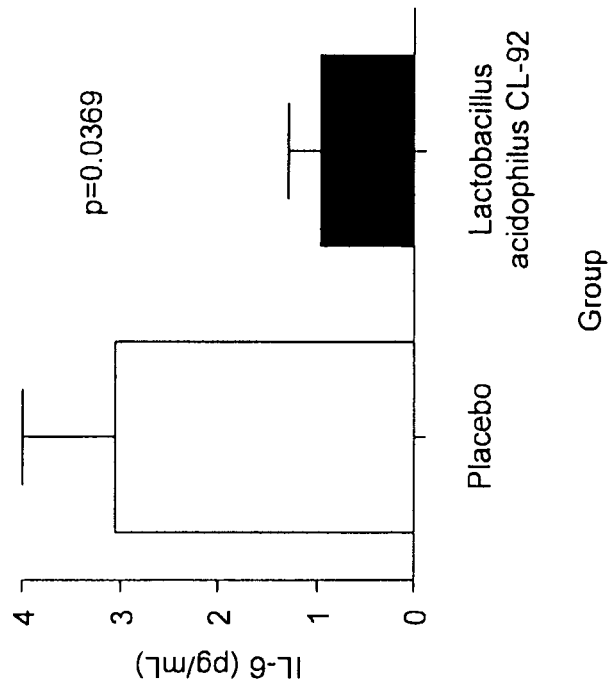
FIG. 7 is a graph showing the inflammation-suppressing effect of the intake of *Lactobacillus acidophilus* CL-92 strain cells, on each concentration of blood plasma FGF-basic (also referred to as "b-FGF") (A) and blood plasma IL-6 (B) in a rheumatoid arthritis model at the end of the experiment.
Figure 7:
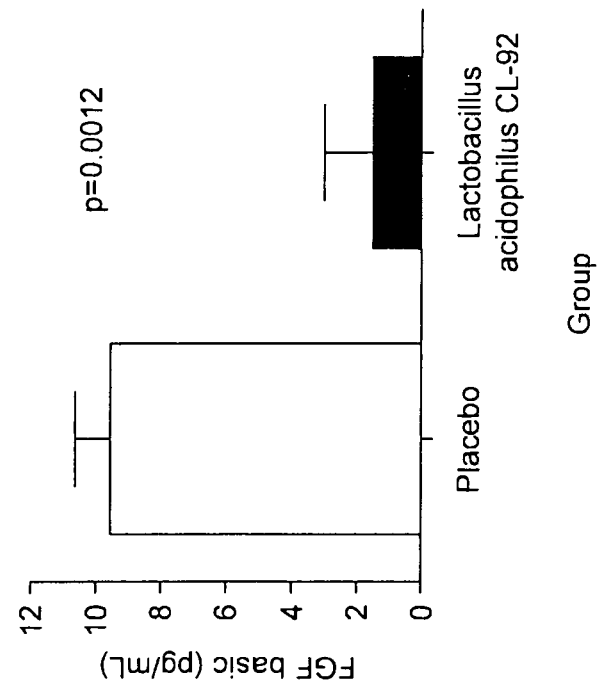

With the use of a Mouse Cytokine Twenty-Plex Antibody Beads Kit (Invitrogen) and blood plasma obtained at the time of autopsy, the effect of the lyophilized powder of the *Lactobacillus acidophilus* CL-92 strain on the expression of inflammatory cytokines was determined. As a result, in contrast to the results for a control substance (non-anti-inflammatory), significantly suppressed expression of FGF-basic and IL-6 (statistical significance (p): 0.00012 and 0.0369, respectively) were observed (FIG. 7A and FIG. 7B). These cytokines are involved both in acceleration of joint synovial growth and in acceleration of inflammation, and they are associated with suppression of footpad hypertrophy.

<Changes Over Time in Blood Plasma Cytokine Levels>

Figure 8:
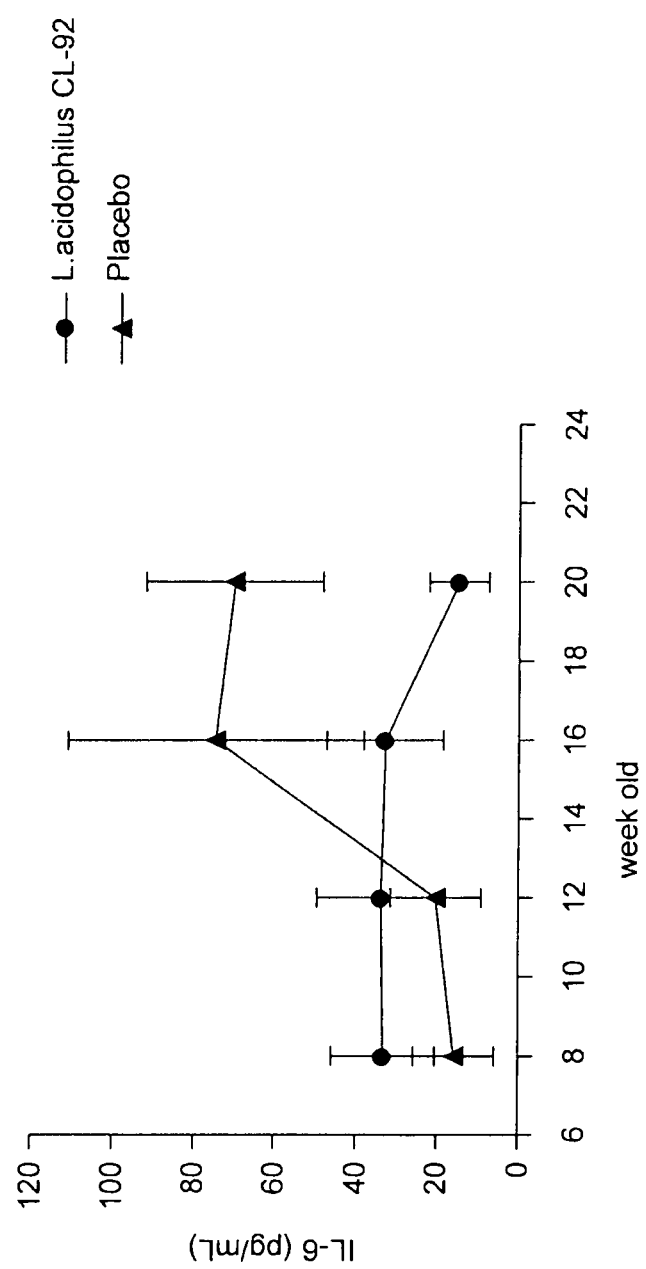
FIG. 8 is a graph showing the degree of the effect of the intake of *Lactobacillus acidophilus* CL-92 strain cells, on changes over time in the concentration of blood plasma IL-6 in a rheumatoid arthritis rat model.

Changes over time in blood plasma IL-6 level were examined to support the expression of the effect of suppressing inflammation. As shown in FIG. 8, blood plasma IL-6 levels during weeks 8, 12, 16, and 20 were measured. It was revealed that IL-6 induction was completely inhibited by the administration of the *Lactobacillus acidophilus* CL-92 strain. Tocilizumab antibody against IL-6 receptor has been developed as a medicament and plays an important role in the treatment of rheumatism. Accordingly, the effect of suppressing inflammation indicates a new possibility of lactic acid bacteria.

<DNA Array Analysis of Spleen>

The spleens of 5 mice, each of which had exhibited results close to the average for each group, were subjected to DNA array analysis. Op Array™ MouseV4.0 (Operon Biotechnologies) was used as a DNA array and then comparative analyses were conducted by a monochromatic method. As a result, significantly elevated Stat3 levels were observed, indicating that the IL-10 signal and the like had suppressed the activity of effector cells involved in inflammation. Moreover, suppressed expression levels were confirmed for inflammation and autoimmune-disease-related genes such as Mapk1, Traf2, Casp2, and Nfatc3.

Furthermore, suppressed activation of antigen presenting cells such as dendritic cells and macrophages was suggested (Table 4). Suppressed Vegf production and suppressed tissue metalloprotease (Metarujidin: Adam-15) level were observed, and thus the suppression of rheumatoid arthritis was supported. Moreover, the expression of Cd40lg involved in Th activation was suppressed, suggesting the suppression of inflammatory signals.

<DNA Array Analysis of Peyer's Patch>

In a manner similar to that for spleens, the Peyer's patches (PP) of the same 5 mice were subjected to DNA array analyses. DNA array analyses were conducted using procedures similar to the above. As a result, suppressed expression of genes involved in activation of the natural immune system was confirmed. The expression of IGHA, IGHV, IL-4, and the like was enhanced, resulting in accelerated IgA production. The thus secreted IgA functions to eliminate harmful substances such as viruses, bacteria, bacterial toxins, and allergens that enter intestinal tracts or other mucosal tissues. As observed in the case of increased expression of Defcr5, Defensin production was also increased. It was understood based on these results that the protective function of the mucous membrane was significantly enhanced.

Furthermore, the expression of IL22 and that of IL22ra1 were also suppressed, indicating that Th17, which is involved in induction of inflammation, might be suppressed (Table 3).

TABLE 3

DNA array analysis in spleen and Peyer's patch

| Organ | Pathway | Gene | Multi-plying factor | Significance (p) |
|---|---|---|---|---|
| Spleen | MAP kinase signal transduction | Mapk1 | 0.693 | 0.005 |
| | NF-κB signal transduction | Traf2 | 0.523 | 0.037 |
| | Apoptosis | Casp2 | 0.637 | 0.031 |
| | Autoimmunity | Nfatc3 | 0.544 | 0.012 |
| | | Vegfc | 0.668 | 0.035 |
| | | Vegfa | 0.671 | 0.036 |
| | | Adam15 | 0.654 | 0.012 |
| | Dendritic cell & APC | Stat3 | 1.979 | 0.009 |
| | Th | Cd40lg | 0.659 | 0.076 |
| Peyer's patch | Th17 | Il22 | 0.527 | 0.002 |
| | | Il22ra1 | 0.579 | 0.024 |
| | IgA | IGHA | 1.861 | 0.004 |
| | | IGKV14-130 | 3.068 | 0.008 |
| | | Il4 | 1.419 | 0.055 |
| | | Ifng | 0.537 | 0.005 |
| | Defensing | Defcr5 | 3.521 | 0.003 |
| | Dendritic cell & APC | Fas | 1.529 | 0.005 |
| | | Cxcl16 | 1.735 | 0.013 |

Example 6

<Selection of Lactic Acid Bacteria Having High Effect of Suppressing Arthritis in Rheumatoid Arthritis Mouse Model>

The *Lactobacillus rhamnosus* SP1 strain (undisrupted) that had exhibited a general effect of suppressing adjuvant arthritis and the *Lactobacillus acidophilus* CL-92 strain (undisrupted) that had exhibited a strong effect of the same were compared, for example, by the procedures described in Example 5 using a rheumatoid arthritis mouse model, in order to select anti-inflammatory lactic acid bacteria.

Figure 9:
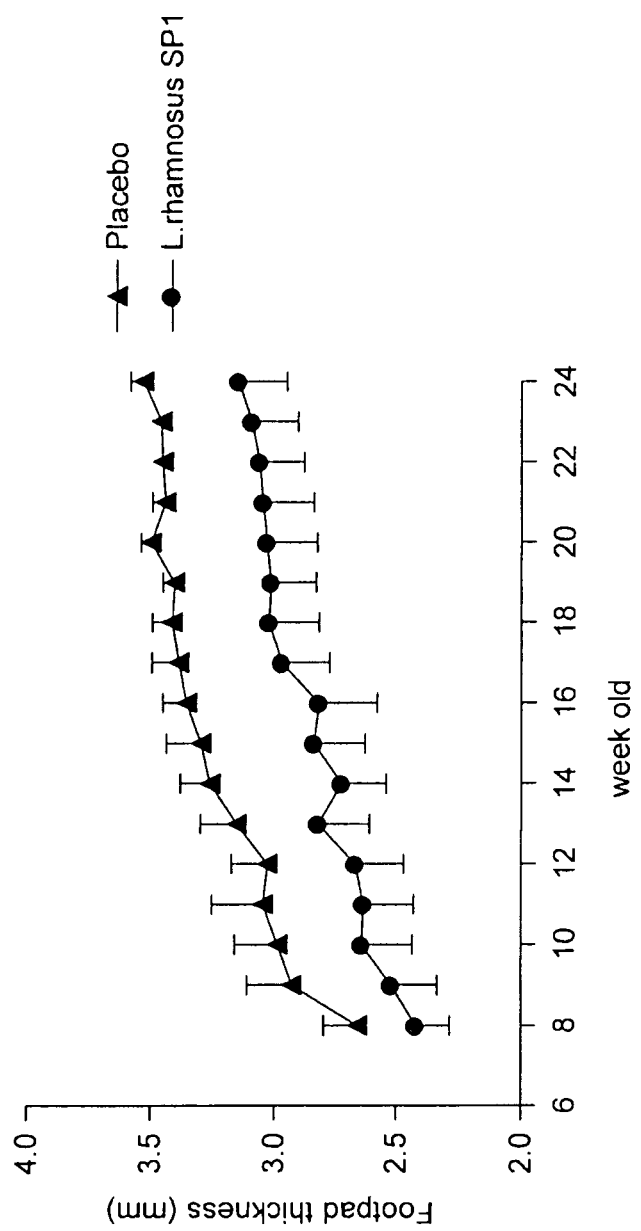
FIG. 9 is a graph showing the degree of the effect of the intake of *Lactobacillus rhamnosus* SP 1 strain cells in a rheumatoid arthritis rat model, using the size of hypertrophy of rat footpads as an indicator.

FIG. 9 and FIG. 6 (described above) show changes in average hypertrophy volume of the foot pads of left and right hindlimbs. As demonstrated in screening for adjuvant arthritis, the superiority of the *Lactobacillus acidophilus* CL-92 strain was indicated. As revealed by statistical analysis, the superiority of the *Lactobacillus acidophilus* CL-92 strain was clear in terms of both differences among groups and the pattern of change (Table 4: repeatedly measured results of the mixed model analysis of variance). Thus, the necessity of selecting lactic acid bacteria having a high anti-inflammatory effect was also suggested in case of the rheumatoid arthritis model.

TABLE 4

Repeatedly measured results of the
mixed model analysis of variance

| | | Lactic acid bacteria | |
|---|---|---|---|
| Factors | | L. acidophilus CL-92 | L. rhamnosus SP1 |
| Primary | Group | 0.009 | 0.033 |
| Secondary | Time | 0.060 | 0.000 |
| | Time x group | 0.008 | 0.812 |

INDUSTRIAL APPLICABILITY

According to the present invention, a substance containing disrupted cells of an anti-inflammatory lactic acid bacterium and having the effect of improving articular inflammation, a composition containing the substance, and use thereof are provided. The substance and the composition of the present invention can improve, ameliorate, suppress, or normalize articular inflammation, and particularly symptoms mainly affecting knee joints; thus, the substance and the composition can be used for preventing or treating various articular inflammatory diseases or disorders. Therefore, the present invention is useful in the fields of medicaments, foods or drinks, stockbreeding, the pet industry, and the like.

All publications, patents, and patent applications cited herein are incorporated herein by reference in their entirety.

The invention claimed is:

1. A method for improving one or more symptoms of arthritis in a subject in need thereof comprising:
    (a) disrupting cells of a lactic acid bacterium to produce a composition comprising disrupted cells of the lactic acid bacterium;
    (b) administering an effective amount of the composition to the subject, wherein the average long diameter and/or surface area of each disrupted cell is 90% or less of that of the lactic acid bacterial cells before disruption.

2. The method of claim 1, wherein the disrupting step is conducted via physical disruption, chemical treatment, or enzymatic lysis.

3. The method of claim 1, wherein the lactic acid bacterium is *Lactobacillus acidophilus* CL-92 strain (FERM BP-4981), *Lactobacillus amylovorus* CP1563 strain (FERM BP-11255) or *Lactobacillus gasseri* CP2305 strain (FERM BP-11331), or a mutant strain thereof or derived strain therefrom.

4. The method of claim 1, wherein the arthritis is rheumatoid arthritis, knee osteoarthritis, tenosynonitis, periomarthritis, tendinitis, or coxitis.

5. The method of claim 1, wherein the lactic acid bacterium is at least one bacterium belonging to a genus selected from the group consisting of the genera *Lactobacillus*, *Bifidobacterium*, *Enterococcus*, *Leuconostoc*, *Streptococcus*, *Lactococcus*, *Pediococcus*, and *Weissella*.

6. The method of claim 5, wherein the bacterium belonging to the genus *Lactobacillus* is at least one bacterium selected from the group consisting of *Lactobacillus amylovorus*, *Lactobacillus gasseri*, *Lactobacillus casei*, *Lactobacillus paracasei*, *Lactobacillus zeae*, *Lactobacillus rhamnosus*, *Lactobacillus reuteri*, *Lactobacillus acidophilus*, *Lactobacillus crispatus*, *Lactobacillus gallinarum*, *Lactobacillus brevis*, *Lactobacillus fermentum*, *Lactobacillus plantarum*, *Lactobacillus delbrueckii subsp. bulgaricus*, and *Lactobacillus johnsonii*.

7. The method of claim 1, further comprising adding at least one known substance having an anti-inflammatory effect to the composition.

8. The method of claim 7, wherein the known substance having an anti-inflammatory effect is collagen, glucosamine, chondroitin, fatty acid, amino acid, or a salt thereof, or a combination thereof.

9. The method of claim 8, wherein the combination is with glucosamine or a salt thereof and chondroitin or a salt thereof.

10. A method for decreasing IL-6 expression in a subject in need thereof comprising:
    (a) disrupting cells of a lactic acid bacterium to produce a composition comprising disrupted cells of the lactic acid bacterium;
    (b) administering an effective amount of the composition to the subject, wherein the average long diameter and/or surface area of each disrupted cell is 90% or less of that of the lactic acid bacterial cells before disruption.

11. The method of claim 10, wherein the lactic acid bacterium is *Lactobacillus acidophilus* CL-92 strain (FERM BP-4981), *Lactobacillus amylovorus* CP1563 strain (FERM BP-11255) or *Lactobacillus gasseri* CP2305 strain (FERM BP-11331), or a mutant strain thereof or derived strain therefrom.

12. The method of claim 10, wherein the lactic acid bacterium is at least one bacterium belonging to a genus selected from the group consisting of the genera *Lactobacillus*, *Bifidobacterium*, *Enterococcus*, *Leuconostoc*, *Streptococcus*, *Lactococcus*, *Pediococcus*, and *Weissella*.

13. The method of claim 12, wherein the bacterium belonging to the genus *Lactobacillus* is at least one bacterium selected from the group consisting of *Lactobacillus amylovorus*, *Lactobacillus gasseri*, *Lactobacillus casei*, *Lactobacillus paracasei*, *Lactobacillus zeae*, *Lactobacillus rhamnosus*, *Lactobacillus reuteri*, *Lactobacillus acidophilus*, *Lactobacillus crispatus*, *Lactobacillus gallinarum*, *Lactobacillus brevis*, *Lactobacillus fermentum*, *Lactobacillus plantarum*, *Lactobacillus delbrueckii subsp. bulgaricus*, and *Lactobacillus johnsonii*.

* * * * *